United States Patent
Graczyk et al.

(10) Patent No.: US 7,652,137 B2
(45) Date of Patent: Jan. 26, 2010

(54) SYNTHESIS OF 5 SUBSTITUTED 7-AZAINDOLES AND 7-AZAINDOLINES

(75) Inventors: Piotr Pawel Graczyk, London (GB); Afzal Khan, London (GB); Gurpreet Singh Bhatia, London (GB)

(73) Assignee: Eisai R & D Management Co., Ltd. (JP)

( * ) Notice: Subject to any disclaimer, the term of this patent is extended or adjusted under 35 U.S.C. 154(b) by 450 days.

(21) Appl. No.: 10/548,162

(22) PCT Filed: Mar. 5, 2004

(86) PCT No.: PCT/GB2004/000946

§ 371 (c)(1),
(2), (4) Date: Mar. 13, 2006

(87) PCT Pub. No.: WO2004/078757

PCT Pub. Date: Sep. 16, 2004

(65) Prior Publication Data

US 2006/0235042 A1    Oct. 19, 2006

(30) Foreign Application Priority Data

Mar. 6, 2003   (GB)   ................ 0305142.2

(51) Int. Cl.
C07D 471/04 (2006.01)
(52) U.S. Cl. ........................ 546/14; 546/113
(58) Field of Classification Search ........... 546/14, 546/113
See application file for complete search history.

(56) References Cited

U.S. PATENT DOCUMENTS

| | | |
|---|---|---|
| 4,719,218 A | 1/1988 | Bender et al. |
| 5,439,917 A | 8/1995 | Briving et al. |
| 5,714,495 A | 2/1998 | Viaud et al. |
| 6,642,375 B2 | 11/2003 | Inomata et al. |
| 7,291,630 B2 | 11/2007 | Graczyk et al. |
| 7,314,940 B2 | 1/2008 | Graczyk et al. |
| 2002/0013354 A1 | 1/2002 | Cheng et al. |
| 2005/0272761 A1 | 12/2005 | Graczyk et al. |
| 2006/0235042 A1 | 10/2006 | Graczyk et al. |
| 2006/0270646 A1 | 11/2006 | Graczyk et al. |
| 2007/0072896 A1 | 3/2007 | Khan et al. |

FOREIGN PATENT DOCUMENTS

| | | |
|---|---|---|
| EP | 0509974 | 10/1992 |
| EP | 0 737 685 | 10/1996 |
| EP | 1 106 621 | 6/2001 |
| JP | 06247966 | 9/1994 |
| WO | WO-92/10498 A1 | 6/1992 |
| WO | WO-92/10499 A1 | 6/1992 |
| WO | WO-98/47899 | 10/1998 |
| WO | WO-99/20624 | 4/1999 |
| WO | WO-99/21859 | 5/1999 |
| WO | WO-99/51233 | 10/1999 |
| WO | WO-00/26210 | 5/2000 |
| WO | WO-00/26211 | 5/2000 |
| WO | WO-00/35909 | 6/2000 |
| WO | WO-00/35921 A1 | 6/2000 |
| WO | WO-00/43393 | 7/2000 |
| WO | WO-00/56710 | 9/2000 |
| WO | WO-00/64449 | 11/2000 |
| WO | WO-00/64872 | 11/2000 |
| WO | WO-01/12609 | 2/2001 |
| WO | WO-01/47922 | 7/2001 |
| WO | WO-01/49288 | 7/2001 |
| WO | WO-02/10137 | 2/2002 |
| WO | WO-02/16359 | 2/2002 |
| WO | WO-02/081475 | 10/2002 |
| WO | WO-03/028724 | 4/2003 |
| WO | WO-03/082868 | 10/2003 |
| WO | WO-03/082869 | 10/2003 |
| WO | WO-2004/016609 | 2/2004 |
| WO | WO-2004/016610 | 2/2004 |
| WO | WO-2004/078756 | 9/2004 |

OTHER PUBLICATIONS

Denmark et al., "Convergence of Mechanistic Pathways in the Palladium(0)-Catalyzed Cross-Coupling of Alkenylsilacyclobutanes and Alkenylsilanols", *Organic Letters*. vol. 2, No. 16, pp. 2491-2494. (2000).

Denmark et al., "Highly Stereospecific, Palladium-Catalyzed Cross-Coupling of Alkenylsilanols" *Organic Letters* vol. 2, No. 4, pp. 565-568 (2000).

Greene, T. and Wuts, P., *Protective Groups in Organic Synthesis*, 3rd Edition, Wiley, New York (1999).

Hatanaka et al., "Cross-Coupling of Organosilanes with Organic Halides Mediated by Palladium Catalyst and Tris(diethylamino)sulfonium Difluorotrimethylsilicate" *J. Org. Chem* 53 pp. 918-920 (1988).

(Continued)

*Primary Examiner*—Patricia L Morris
(74) *Attorney, Agent, or Firm*—Wilmer Cutler Pickering Hale & Dorr LLP.

(57) ABSTRACT

The present invention provides a novel substituted azaindoline intermediate of formula (I) and a method for its synthesis. The novel substitued azaindoline intermediate (I) is provided for use in the manufacture of 5-substituted 7-azaindolines and 5-substituted 7-azaindoles.

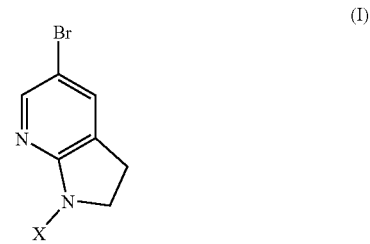

(I)

9 Claims, No Drawings

Hatanaka et al., "Highly Selective Cross-Coupling Reactions of Organosilicon Compounds Mediated by Fluoride Ion and a Palladium Catalyst", *Synlett* pp. 845-853 (1991).

Krasnokutskaya et al., *Khim. Geterotsikl. Soed* No. 3 pp. 380-384 (1977).

Littke et al., "Versatile Catalysts for the Suzuki Cross-Coupling of Arylboronic Acids with Aryl and Vinyl Halides and Triflates under Mild Conditions" *J. Am. Chem. Soc.* 122 pp. 4020-4028 (2000).

Littke et al., "Pd/P(t-Bu)$_3$: A Mild and General Catalyst for Stille Reactions of Aryl Chlorides and Aryl Bromides" *J. Am. Chem. Soc.* 124 pp. 6343-6348 (2002).

Martin et al., "Palladium-Catalyzed Cross-Coupling Reactions of Organoboronic Acids with Organic Electrophiles" *Acta Chemica Scandinavica* 47, pp. 221-230 (1993).

Merour et al., Synthesis and Reactivity of 7-Azaindoles (1H-Pyrrolo[2,3-b]pyridine) *Current Organic Chemistry* 5 pp. 471-506 (2001).

Mitchell, T. "Palladium-Catalysed Reactions of Organotin Compounds" *Synthesis* pp. 803-815 (1992).

Stille, J.K,. "The Palladium-Catalyzed Cross-Coupling Reactions of Organotin Reagents with Organic Electrophiles" *Angew. Chem. Int. Ed. Engl.* 25 pp. 508-524 (1986).

Suzuki, A. "Synthetic Studies via the Cross-Coupling Reaction of Organoboron Derivatives with Organic Halides" *Pure Appl. Chem* vol. 63, No. 3 pp. 419-422 (1991).

Tamao et al., "Palladium-Catalyzed Cross-Coupling REaction of Alkenylalkosysilanes with Aryl and Alkenyl Halides in the Presence of a Fluoride Ion" *Tetrahedron Letters*, vol. 30, No. 44 pp. 6051-6054 (1989).

Taylor et al., "Intramolecular Diels-Alder Reactions of 1,2,4-Triazines" *Tetrahedron*, vol. 43, No. 21 pp. 5145-5158 (1987).

U.S. Appl. No. 10/591,551.

U.S. Appl. No. 12/143,231.

Adams et al. , Bioorg. Med. Chem. Lett. 2001, 11, 2867-2870.

Alam et al., Synthesis and SAR of aminopyrimidines as novel c-Jun N-terminal kinase (JNK) inibitors:, Bioorg Med Chem Lett, vol. 17, pp. 3463-3467, 2007.

Bundgaard, Design of ProDrugs, Elsevier Science Publishers 1985.

Cao et al., "Distinct Requirements for p38α and c-Jun N-terminal Kinase Stress-activated Protein Kinases in Different Forms of Apoptotic Neuronal Death", *The Journal of Biological Chemistry*, vol. 279, No. 34, pp. 35903-35913, Aug. 20 ,2004.

CAS Accession No. 2001:432896, Registry No. 344454-31-1.

CAS Document No. 135:107148.

CAS document No. 135:43132.

Corey, E.Jr., et. al.., A synthetic Method for Formyl-Ethynyl Conversion (RCHO—RC=CH or RC=CR'), Tetrahedron Letters No. 36, Aug. 1972.

Database Beilstein, Beilstein Institute for Organic Chemistry, Citation No. 5563002 (1987).

Dhar, et al., "The TosMIC Approach to 3-(Oxazol-5-yl) Indoles: Application to the Synthesis of Indole-Based IMPDH Inhibitors," Bioorganic & Medicinal Chemistry Letters, 2002.

Eilers et al., "Direct Inhibition of c-Jun N-terminal Kinase in Sympathetic Neurones Prevents c-jun Promoter Activation and NGF Withdrawal-induced Death", *Journal of Neurochemistry*. vol. 76, pp. 1439-1454, 2001.

Eilers et al., "Role of the Jun Kinase Pathway in the Regulation of c-Jun Expression and Apoptosis in Sympathetic Neurons", *The Journal of Neuroscience*. vol. 18, No. 5, pp. 1713-1724, Mar. 1, 1998.

Estus et al., "Aggregated Amyloid-β Protein Induces Cortical Neuronal Apoptosis and Concomitant "Apoptotic" Pattern of Gene Induction", *The Journal of Neuroscience*, vol. 17, No. 20, pp. 7736-7745, Oct. 15, 1997.

Golub et al., Science, vol. 286, pp. 531-537 Oct. 15, 1999.

Guillard, et al. "Synthesis of New Maltonin Analogues from Dimers of Azaindole and Indole by Use of Suzuki Monocoupling", Heterocycles, vol. 60, No. 4, pp. 865-877 (2003).

Ham et al., "A c-Jun Dominant Negative Mutant Protects Sympathetic Neurons against Programmed Cell Death", *Neuron*, Vol. 14, pp. 927-939, May 1995.

Harper and LoGasso, *Drugs of the Future* 2001, 26, 957-973.

Harper et al., "Inhibitors of the JNK Signaling Pathway", *Drugs of the Future*, vol. 26, No. 10, pp. 957-973, 2001.

Henry et al , Bioorg. Med. Chem. Lett. 1998, 8, 3335-3340.

Houwing, et al., Preparation of N-Tosylmethylimino Compounds and their Use in the Synthesis of Oxazoles, Imidazoles and Pyrroles, Tetrahedron Letters No. 2, 1976.

International Search Report for PCT/GB2004/002099, mailed Dec. 2, 2004, 4 pages.

International Search Report for PCT/GB2005/000779, mailed Aug. 12 , 2005, 4 pages.

Kruber, Caplus, Copyright 2007 ACS on STN, 2 pages.

Kumar et al, "Synthesis of 7-Azaindole and 7-Azaoxindole Derivatives through a Palladium-Catalyzed Cross Coupling Reaction", J. Org. Chem, 57, pp. 6995-6998 (1992).

Lecointe, Reach-trhough Claims, International Pharmaceutical (2002)(also available at <http:////www.bakerbotts.com/infocenter/publications/detail.aspx?id=bffe4a7d-5beb-4cf8-a189-15a190f0eb>).

Lisnock et al., "Activation of JNK3α1 Requires Both MKK4 and MKK7: Kinetic Characterization of in Vitro Phosphorylated JNK3α1", *Biochemistry*, vol. 39, pp. 3141-3149, 2000.

Mettey, et al., "Aloisines, a New Family of CDK/GSK-3 Inhibitors. SAR STudy, Crystal Structure in Complex with CDK2, Enzyme Selectivity and Cellular Effects", J. Med. Chem, 46, pp. 222-236 (2003).

Park et al, "A FAcile Synthesis of 2,3-Disubstitute Pyrrolo[2,3-b]pyridines via Palladium-Catalyzed Heteroannulation with Internal Alkynes", Tetrahedron Letters 39, pp. 627-630 (1998).

Pisano et al, "Bis-indols: a Novel Class of Molecules Enhancing the Cytodifferentiating Properties of Retinoids in Myeloid Leukemia Cells", Blood, vol. 100, No. 10, pp. 3719-3730 (2002).

Resnick, et al. "Targeting JNK3 for the Treatment of Meurodegenerative Disorders", Drug Discovery Today, Elsevier Science LTD. 9:21 (2004) pp. 932-939.

Silva, "Reach through Claims: Bust or Boon?", Intellectual Property Update (available at <http://www.dorsey.com/publlications/legal_detail.aspx?FlashNavID=pubs_legal&pubid=170565003>).

Smulik and Diver, "Synthesis of Cyclosporin A-Derived Affinity Reagents by Olefin Metathesis", Organic Letters, vol. 4, No. 12, pp. 2051-2054, 2002.

Van Leusen, et al., Chapter 3: Synthetic Uses of Tosylmethyl Isocyanide (TosMIC), Organic Reactions, vol. 57, 2001.

Vippagunta et al., "Crystalline Solids", Advanced Drug Delivery Reviews, vol. 48, No. 1; pp. 3-26, 2001.

Watson et al., "Phosphorylation of c-Jun is Necessary for Apoptosis Induced by Survival Signal Withdrawal in Cerebellar Granule Neurons", *The Journal of Neuroscience*, vol. 18, No. 2, pp. 751-762, Jan. 15, 1998.

West, Anthony R., "Solid State Chemistry and its Applications", Wiley, NY 1988.

Witherington et al., "5-Aryl-pyrazolo [3,4-b]pyridines: Potent Inhibitors of Glycogen Synthase Kinase-3 (GSK-3)", Bioorganic & Medicinal Chemistry Letters 13, pp. 1577-1580 (2003).

Young et al., "Pyridinyl Imidazole Inhibitors of p38 Mitogen-activated Protein Kinase Bind in the ATP Site", *The Journal of Biological Chemistry*, vol. 272, No. 18, pp. 12116-12121, May 2, 1997.

Zevaco, T. et al., Bismuth (III) Pyridine—and Pyrazine-Carboxylates, *New J. Chem*.., vol. 15, pp. 927-930, 1991.

Kontoyiannis et al., "Imparied On/Off Regulation of TNF Biosynthesis in Mice Lacking TNF AU-Rich Elements: Implications for Joint and Gut-Associated Immunopathologies", Immunity, (1999 Mar) vol. 10, pp. 387-398.

Leroy et al., "Homochiral NADH models in the pyrrolo[2,3-b]pyridine series bearing one or two chiral auxiliaries. Asymmetric reduction of methyl benzoylformate and N-acetyl-enamines. Influence of the magnesium salt concentration on the asymmetric induction of reductions." Tetrahedron: Asymmetry, vol. 8, No. 19, pp. 3309-3318, 1997.

Han, Z. et al., "Jun N-Terminal Kinase in Rheumatoid Arthritis," J. of Pharmacol. Exper. Therap. 291(1): 124-130 (1999).

Kontoyiannis et al., Immunity, (1999 Mar) vol. 10, No. 3, pp. 387-398.

Leroy et al., Tetrahedron: Asymmetry (1997), 8(19), 3309-3318.

Peng, J. and Andersen, J.K., "The Role of c-Jun N-Terminal Kinase (JNK) in Parkinson's Disease," Life 55(4-5): 267-271, Apr.-May 2003.

SYNTHESIS OF 5 SUBSTITUTED 7-AZAINDOLES AND 7-AZAINDOLINES

The present invention provides a novel substituted azaindoline intermediate and a method for its synthesis. The invention further provides the use of the intermediate in the manufacture of 5-substituted 7-azaindolines and 5-substituted 7-azaindoles.

The 7-azaindole system forms the core structure of various pharmaceutically important substances such as antitumour agents, ligands of melatoninergic receptor, dopamine $D_4$ receptors, serotonin receptor, 5-HT6 receptor, p38 kinase inhibitors, renin inhibitors, thrombin inhibitors, and antitussive agents. Furthermore, antifungal activity of some 7-azaindoles in plant systems has recently been discovered.

Synthesis and reactivity of 7-azaindoles has recently been extensively reviewed (Merour and Joseph *Current Org. Chem.* 2001, 5, 471). Functionalization of the 7-azaindole system at position 5 is a fundamental transformation used in the synthesis of melatoninergic ligands and JNK inhibitors. Such functionalization is achieved by initial installation of the bromine atom at position 5, which is considered to be the key step in each of these synthetic routes. However, despite the importance of this process, the most widely used approach to introduce the bromine atom in position 5 requires dibromide (2) as an intermediate (Scheme 1). The two bromine atoms at C(3) serve as temporary and expensive temporary protection against bromination of the five-membered ring.

Synthesis of dibromide (2) is troublesome due to the use of large excess of pyridinium perbromide (4 equivalents) and difficult workup procedure. If direct conversion of (1) into (3) is undertaken, large excess of bromine—usually over 12 molar equivalents is required.

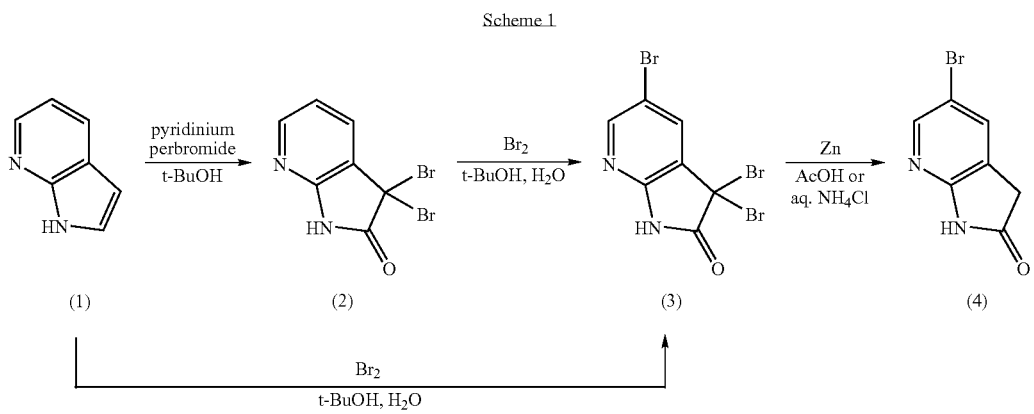

Scheme 1

Furthermore, the subsequent reductive debromination of (3) to afford (4) is conducted with 10-fold excess of zinc in acetic acid or excess of saturated aqueous solution of ammonium chloride, which results in difficult workup and creation of large amount of waste. Compound (4), thus prepared has limited applicability for further functionalizations.

The transformations known in the art are presented schematically in Scheme 2. Compound (4) can be converted to 5-bromo-7-azaindole (6) via 5-bromo-7-azaindoline (5) and then to the relevant 5-methoxy derivative (7), and may also undergo palladium-catalyzed Suzuki and Stille couplings and carbonylation to afford (8), (9), and (10), respectively.

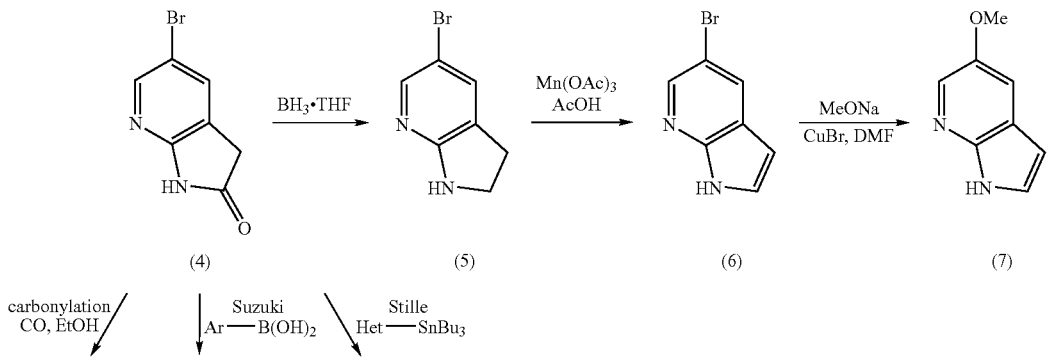

Scheme 2

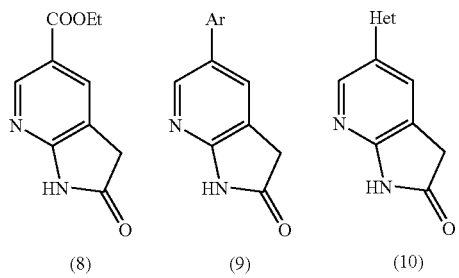

It should be emphasized that reactivity of 5-bromo-7-azaindole (6) in the palladium-catalysed coupling reactions like Suzuki and Stille reactions has not been reported, yet.

Sometimes the problems with installation of substituents at position 5 of the 7-azaindole system are circumvented by linking the desired group to the pyridine ring and subsequently closing the pyrrole ring to form the 7-azaindole system as shown below in Scheme 3 (X is usually halogen).

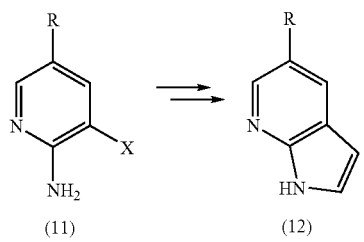

A similar method leading to the 7-azaindoline system (14) (which may be converted to the 7-azaindole skeleton) is based on the intramolecular Diels-Alder reaction of properly functionalised amino pyrimidines (13) (Scheme 4; R=H, NO$_2$).

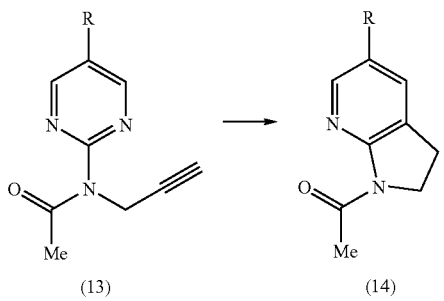

Diels-Alder reaction of properly functionalised 1,2,4-triazines (15) (Scheme 5) may also lead to the 7-azaindoline skeleton (16), but the method works best in the absence of substituent at C(5), i.e. R=H.

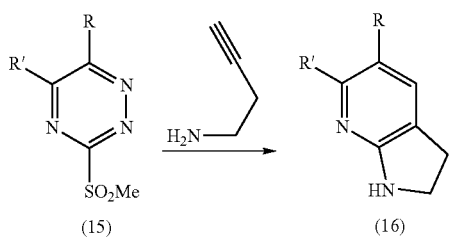

These processes involve many synthetic steps, utilize difficult to synthesize intermediates and/or costly palladium catalysts. Furthermore, all the methods described above allow only a limited scope of substituents to be introduced at C(5). For instance, many substituents easily accessible via carboanion chemistry, like —CH(O)R, —SiR$_3$, —SnR$_3$, have not been explored at all due to unavailability of synthetic methodology leading to 5-lithio-7-azaindole/azaindoline.

Synthesis of the unsubstituted 7-azaindoline starting material has previously involved harsh conditions. Previous attempts to obtain the 7-azaindoline has involved high pressure hydrogenation of 7-azaindole at 200° C., hydrogenation over Pd/δ-Al$_2$O$_3$ at 150° C. and under 450 psi pressure and hydrogenation over Pd/C in neat trifluoroacetic acid under 50 psi. Such reduction methods are hindered as the hydrogenolysis of 7-azaindole in the acidic medium catalysed by PtO$_2$ may lead to overreduction Derivatisation of the 7-azaindoline system obtained by the methods above is limited. Subsequent bromination of 7-azaindoline system (17) (Scheme 6) using dioxane dibromide, NBS or bromine to give bromide (5) is known. Limited functionalization of (5) to the cyano derivative (18) has also been presented.

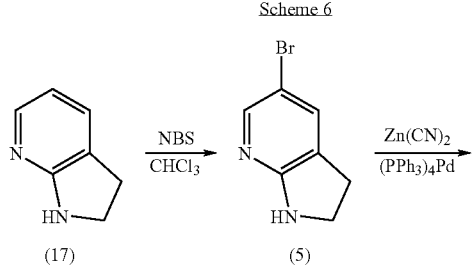

-continued

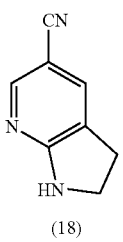

(18)

Similar transformation involving a N-protected azaindoline (19) (Scheme 7) has also been described.

Scheme 7

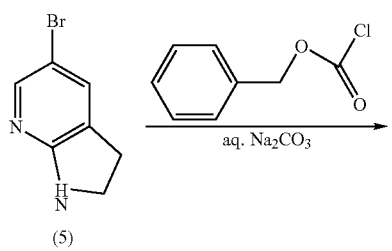

(5)

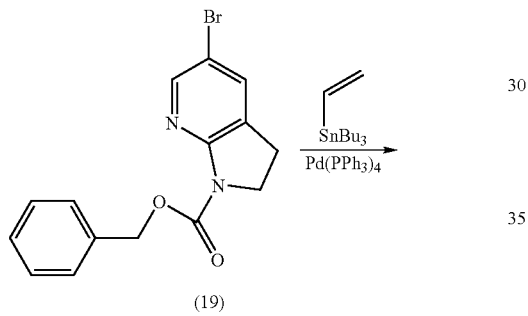

(19)

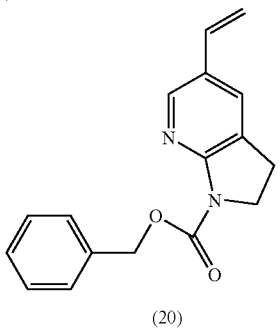

(20)

However, the nitrogen protecting group used in 5-bromo-7-azaindoline (19), benzyloxycarbonyl (Cbz), although easy to install, has a limited resistance. In particular it is unsuitable for reactions involving strong bases such as n-BuLi, sec-BuLi, tert-BuLi, NaNH$_2$, and Grignard reagents. Such reactions, especially with alkyllithiums, could open a novel way for derivatization of the 7-azaindole system at C(5). However, the use of other protecting groups to protect the 5-bromo-7-azaindoline system is unknown in the art.

The production of 5-substituted-7-azaindoles therefore provides a number of problems in the art. There is therefore a need in the art for new methods of preparing such compounds.

To avoid the problems associated with the current state-of-the-art methods and to open new possibilities for functionalization of position 5 of the 7-azaindole system, the present invention provides the use of functionalised 7-azaindoline derivatives as key intermediates. These intermediates can be rearomatized with DDQ to 7-azaindoles avoiding the use of heavy metal oxidants such as Mn(OAc)$_3$ or MnO$_2$ (cf Scheme 2). The ability to avoid the use of heavy metal oxidants is particularly important when the resulting 5-functionalised-7-azaindoles are used in medicine.

Attempts have previously been made to use DDQ for similar purposes. However the obtained yields for rearomatization of unprotected 7-azaindolines were prohibitively low, (i.e. below 50%) indicating that the use of DDQ was not viable in a commercial synthesis (Taylor et al. *Tetrahedron* 1987, 43, 5145). The present invention demonstrates that proper choice of protecting group, in particular the electron-donating silyl group, allows this process to occur in a quantitative yield. The present invention therefore provides a method of rearomatization which can be used on an industrial scale and eliminates unwanted heavy metal residues in the product. Furthermore, the present invention further provides a new, simple method to synthesise the starting unsubstituted 7-azaindoline, which avoids using harsh conditions described in the literature. The present invention therefore provides a significant advance in the production of 5-functionalised-7-azaindoles.

The first aspect of the present invention provides a compound of formula (I)

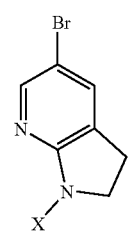

(I)

wherein X is an amino-protecting group, with the proviso that X is not benzyloxycarbonyl (Cbz).

In particular, X is preferably selected from $R^1S(O)_2$, $(R^1)_3Si$, $R^1C(O)$, $R^1OCH_2$, $R^1_2NSO_2$, $R^1OC(O)$—, $R^1(R^1O)CH$—, $R^1CH_2CH_2$—, $R^1CH_2$—, $PhC(O)CH_2$—, $CH_2=CH$—, $ClCH_2CH_2$—, $Ph_3C$—, $Ph_2(4$-pyridyl$)C$—, $Me_2N$—, $HO$—$CH_2$—, $R^1OCH_2$—, $(R^1)_3SiOCH_2$—, $(R^1O)_2CH$—, t-BuOC(O)CH$_2$—, Me$_2$NCH$_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl, with the proviso that when X is $R^1OC(O)$—, $R^1$ is not PhCH$_2$.

When X is a dialkylsulfonamide ($R^1_2NSO_2$—), $R^1$ is preferably alkyl, more preferably methyl. When X is a carbamate ($R^1OC(O)$—) $R^1$ is preferably alkyl, cycloalkyl, aryl or heteroaryl, more preferably CCl$_3$CH$_2$, Me$_3$SiCH$_2$CH$_2$, t-butyl, 2,4-dimethylpent-3-yl, cyclohexyl, CCl$_3$Me$_2$COC(O), 1-adamantyl, 2-adamantyl or cyclohexyl. When X is N-(1-alkoxy)ethylamine ($R^1(R^1O)CH$—), $R^1$ is preferably alkyl, more preferably Me or Et. When X is N-2-(hetero)arylethylamine ($R^1CH_2CH_2$—), $R^1$ is preferably aryl or heteroaryl, more preferably 2-pyridyl, 4-pyridyl or 4-nitrophenyl. When X is arylmethylamine ($R^1CH_2$—), $R^1$ is aryl or heteroaryl, more preferably Ph-, p-methoxyphenyl-, 3,4-dimethoxyphenyl, 3-methoxyphenyl, 3,5-dimethoxyphenyl, 2-nitrophenyl or 2,4-dinitrophenyl. When X is N-alkoxymethylamine (R¹OCH₂—), R¹ is alkyl, more preferably methyl, ethyl, ClCH₂CH₂—, Me₃SiCH₂CH₂—, t-butyl or PhCH₂—.

When X is N-silyloxymethylamine ((R¹)₃SiOCH₂—), R¹ is alkyl, more preferably methyl or t-butyl. When X is N-dialkoxymethylamine ((R¹O)₂CH—), R¹ is alkyl, more preferably methyl or ethyl. When X is sulfonamide (R¹S(O)₂—), R¹ is preferably 2,4,6-trimethylphenyl (mesityl), 4-methoxyphenyl, phenyl or toluyl.

Such protecting groups must not deactivate the pyridine ring towards bromination, and must withstand the conditions of the subsequent reactions, in particular these involving carboanion chemistry. X is therefore most preferably a silyl group (especially t-butyldimethylsilyl (TBS), triisopropylsilyl (TIPS) or t-butyldimethylphenylsilyl (TBDPS)), N-alkoxymethylamine (R¹OCH₂—) wherein R¹ is preferably methyl or a sulfonamide R¹S(O)₂ wherein R¹ is preferably phenyl, methoxymethyl (MOM) or ethoxymethyl.

Compound (I) of the present invention is a versatile intermediate and allows the production of many 5-substituted 7-azaindoles.

The second aspect of the invention provides a method for synthesising a compound of formula (I) comprising brominating a compound of formula (II);

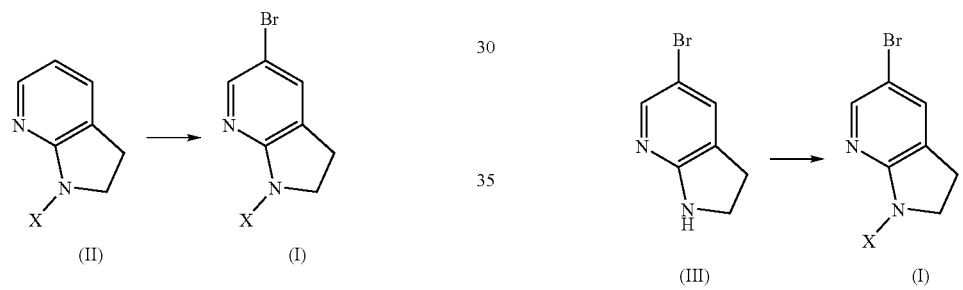

wherein X is a amino-protecting group as defined in the first aspect of the invention.

In a preferred feature of the second aspect, X is preferably selected from (R¹)₃Si or R¹OCH₂, wherein R¹ is C₁₋₆ alkyl or C₆₋₁₂ aryl, preferably methyl, ethyl, propyl n-butyl, tert-butyl or phenyl.

In a preferred feature of the second aspect, X is (R¹)₃Si and R¹ is independently C₁₋₆ alkyl or C₆₋₁₂ aryl, preferably methyl, ethyl, propyl, n-butyl, tert-butyl or phenyl.

Bromination can be carried out using reagents and conditions known in the art. The reagents are preferably Br₂, dioxane dibromide, pyridinium perbromide or NBS.

For the purposes of this invention, a compound of formula (II) can be provided from azaindoline using reagents and methods well known in the art. Protecting groups such as benzyl, acetamide, benzyl carbamate or p-toluenesulfonamide can be installed using standard methods known in the art, which are described in T. W. Greene and P. G. M. Wuts *Protective Groups in Organic Synthesis* 3rd Edn., Wiley, New York 1999; pages 494-626.

Alternatively, the protecting group X can be introduced prior to the formation of the azaindole skeleton, as illustrated below wherein the p-toluenesulfonyl group is linked to the nitrogen of the 7-azaindole system as a result of the reaction between N-tosylaziridine and malonodinitrile (*Chemische Berichte* 1985, 118, 4473).

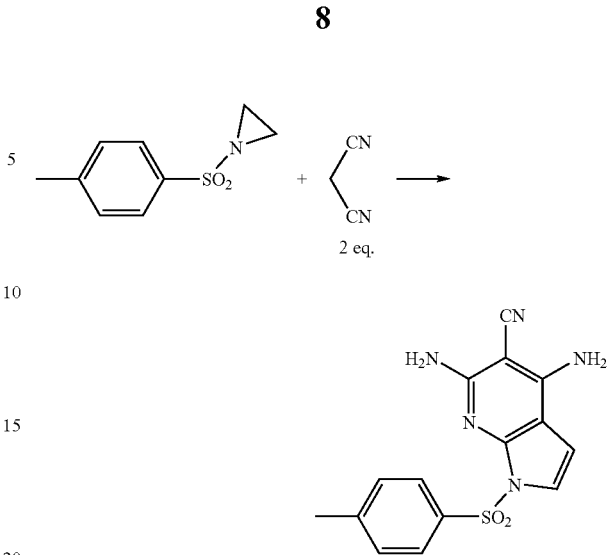

An alternative method of producing a compound of formula (I) involves the protection of a compound of formula (III) as illustrated.

wherein X is selected from R¹S(O)₂, (R¹)₃Si, R¹C(O), R¹OCH₂, R¹₂NSO₂, R¹OC(O)—, R¹(R¹O)CH—, R¹CH₂CH₂—, R¹CH₂—, PhC(O)CH₂—, CH₂=CH—, ClCH₂CH₂—, Ph₃C—, Ph₂(4-pyridyl)C—, Me₂N—, HO—CH₂—, R¹OCH₂—, (R¹)₃SiOCH₂—, (R¹O)₂CH—, t-BuOC(O)CH₂—, Me₂NCH₂— and tetrahydropyranylamine;

wherein R¹ is C₁₋₆ alkyl, C₃₋₁₂ cycloalkyl, C₁₋₆ haloalkyl, C₆₋₁₂ heterocyclyl or C₆₋₁₂ carbocyclyl; optionally substituted with one or more of C₁₋₆ alkyl, Si(R³)₃, OR³, NO₂, CO₂, CO₂R³, halogen, haloalkyl, SR³, CN, NR³COR³, COR¹³CONR³R³, wherein R³ is hydrogen or C₁₋₆ alkyl, preferably R¹ is methyl, ethyl, propyl, n-butyl, tert-butyl or phenyl.

The compound of formula (III) can be produced from azaindoline using reagents and methods well known in the art. Examples of such brominations are indicated in Krasnokutskaya et al. *Khim. Geterotsikl. Soed.* 1977, 3, 380, WO00/26210, WO00/26211, WO00/64449, Taylor et al. *Tetrahedron*, 1987, 43, 5145.

The third aspect of the invention provides a method for the production of a compound of formula (IV)

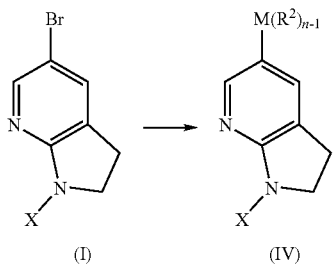

(I)     (IV)

comprising the metal-halogen exchange with a metal of formula $M(R^2)_n$, wherein each $R^2$ is independently OH, $C_{1-6}$ alkyl, $C_{1-6}$ alkoxy, halo or $C_{6-12}$ carbocyclyl, X is selected from $R^1S(O)_2$, $(R^1)_3Si$, $R^1C(O)$, $R^1OCH_2$, $R^1_2NSO_2$, $R^1OC(O)$—, $R^1(R^1O)CH$—, $R^1CH_2CH_2$—, $R^1CH_2$—, $PhC(O)CH_2$—, $CH_2$=CH—, $ClCH_2CH_2$—, $Ph_3C$—, $Ph_2(4\text{-pyridyl})C$—, $Me_2N$—, HO—$CH_2$—, $R^1OCH_2$—, $(R^1)_3SiOCH_2$—, $(R^1O)_2CH$—, t-BuOC(O)$CH_2$—, $Me_2NCH_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl n is 1, 2, 3 or 4, and M is Li, Sn, B, Mg, Zn, In, Cu, Zr, or Pd.

In a preferred feature of the reaction, the compound of formula (IV) may undergo one or more further transmetalation reactions for example by incubation with a metal halide such as $ZnCl_2$, $MgCl_2$, $PdCl_2$, or $(R^2)_3SnW$ wherein $R^2$ is $C_{1-12}$ alkyl, preferably methyl or butyl and W is halogen preferably Cl or I. Preferred examples of metal halides having the formula $(R^2)_3SnW$ include $Bu_3SnI$ or $Me_3SnCl$.

The fourth aspect of the invention provides a compound of formula (IV)

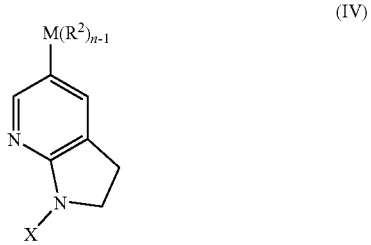

(IV)

wherein each $R^2$ is independently —OH, $C_{1-6}$ alkyl, $C_{1-6}$ alkoxy, halo or $C_{6-12}$ carbocyclyl, n is 1, 2, 3 or 4, M is a metal preferably selected from Li, Sn, B, Mg, Zn, In, Cu, Zr, Pd or Zn and X is a amino-protecting group, preferably selected from $R^1S(O)_2$, $(R^1)_3Si$, $R^1C(O)$, $R^1OCH_2$, $R^1_2NSO_2$, $R^1OC(O)$—, $R^1(R^1O)CH$—, $R^1CH_2CH_2$—, $R^1CH_2$—, $PhC(O)CH_2$—, $CH_2$=CH—, $ClCH_2CH_2$—, $Ph_3C$—, $Ph_2(4\text{-pyridyl})C$—, $Me_2N$—, HO—$CH_2$—, $R^1OCH_2$—, $(R^1)_3SiOCH_2$—, $(R^1O)_2CH$—, t-BuOC(O)$CH_2$—, $Me_2NCH_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl.

In a preferred feature of the fourth aspect, M can represent a metal such as Li, or metal alkyl group such as $Sn(R^2)_3$ wherein $R^2$ is a $C_{1-12}$ alkyl.

The fifth aspect of the invention provides a method for the production of a compound of formula (V)

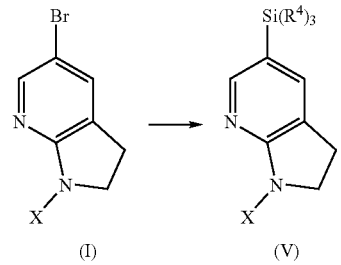

(I)     (V)

comprising incubating a compound of formula (I) with a base and $(R^4)_3SiZ$ wherein $R^4$ is a $C_{1-6}$ alkyl, OH, or an $C_{6-12}$ aryl group, Z is a halide preferably chloride or bromide and X is an amino-protecting group, preferably selected from $R^1S(O)_2$, $(R^1)_3Si$, $R^1C(O)$, $R^1OCH_2$, $R^1_2NSO_2$, $R^1OC(O)$—, $R^1(R^1O)CH$—, $R^1CH_2CH_2$—, $R^1CH_2$—, $PhC(O)CH_2$—, $CH_2$=CH—, $ClCH_2CH_2$—, $Ph_3C$—, $Ph_2(4\text{-pyridyl})C$—, $Me_2N$—, HO—$CH_2$—, $R^1OCH_2$—, $(R^1)_3SiOCH_2$—, $(R^1O)_2CH$—, t-BuOC(O)$CH_2$—, $Me_2NCH_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl.

For the purposes of the fifth aspect, the base is preferably t-BuLi.

The sixth aspect of the invention provides a compound of formula (V)

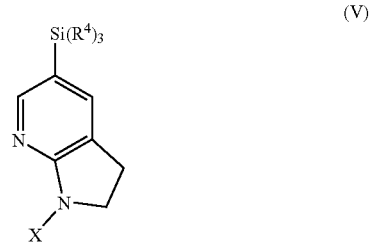

(V)

wherein $R^4$ is a $C_{1-6}$ alkyl, OH, or an $C_{6-12}$ aryl group, X is an amino-protecting group, preferably selected from $R^1S(O)_2$, $(R^1)_3Si$, $R^1C(O)$, $R^1OCH_2$, $R^1_2NSO_2$, $R^1OC(O)$—, $R^1(R^1O)$ CH—, $R^1CH_2CH_2$—, $R^1CH_2$—, $PhC(O)CH_2$—, $CH_2$=CH—, $ClCH_2CH_2$—, $Ph_3C$—, $Ph_2(4\text{-pyridyl})C$—, $Me_2N$—, HO—$CH_2$—, $R^1OCH_2$—, $(R^1)_3SiOCH_2$—, $(R^1O)_2$ CH—, t-BuOC(O)$CH_2$—, $Me_2NCH_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl.

The seventh aspect of the invention provides a method of producing a compound of formula (VI)

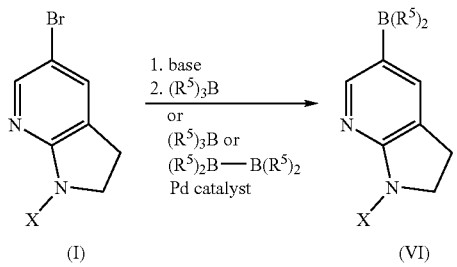

comprising incubating a compound of formula (I) with boronate $(R^5)_3B$, $(R^5)_2B$—H or $(R^5)_2B$—$B(R^5)_2$ and a base or a palladium catalyst such as $PdCl_2$ or $PdCl_2(1,1'$-bis(diphenylphosphino) ferrocene), wherein $R^5$ is OH or a group $OR^{20}$ wherein $R^{20}$ is $C_{1-6}$ alkyl or $C_{6-12}$ aryl and wherein two or more $R^{20}$ groups may together form a 4 to 7 membered ring, and wherein X is an amino-protecting group, preferably selected from $R^1S(O)_2$, $(R^1)_3Si$, $R^1C(O)$, $R^1OCH_2$, $R^1_2NSO_2$, $R^1OC(O)$—, $R^1(R^1O)CH$—, $R^1CH_2CH_2$—, $R^1CH_2$—, $PhC(O)CH_2$—, $CH_2$=CH—, $ClCH_2CH_2$—, $Ph_3C$—, $Ph_2(4$-pyridyl)C—, $Me_2N$—, HO—$CH_2$—, $R^1OCH_2$—, $(R^1)_3SiOCH_2$—, $(R^1O)_2CH$—, t-BuOC(O)$CH_2$—, $Me_2NCH_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl.

More preferably, boronate is selected from H—$B(OR^{15})_2$, $(Me_2C$—$O)_2B$—$B(O$—$CMe_2)_2$ and $B(OR^{15})_3$.

In a preferred feature of the seventh aspect, the production of a compound of formula (VI) can be catalysed by the addition of a metal catalyst. In particular, the formation of a compound of formula (VI) can be catalysed by a palladium catalyst such as $PdCl_2$ or $PdCl_2(1,1'$-bis(diphenylphosphino) ferrocene)

Example of such a boronation reaction is indicated below,

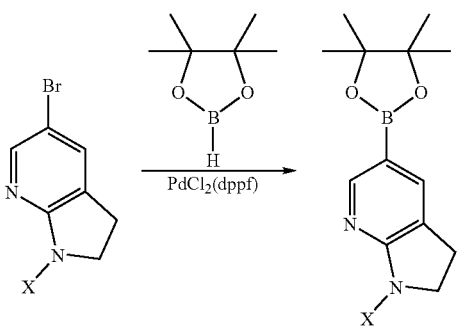

The eighth aspect of the invention provides a compound of formula (VI)

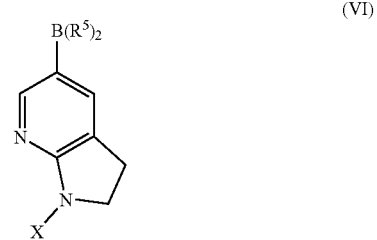

wherein $R^5$ is OH, or a group $OR^{20}$ wherein $R^{20}$ is $C_{1-6}$ alkyl or $C_{6-12}$ aryl and wherein two or more $R^{20}$ groups may together form a 4 to 7 membered ring, and X is a amino-protecting group, preferably selected from $R^1S(O)_2$, $(R^1)_3Si$, $R^1C(O)$, $R^1OCH_2$, $R^1_2NSO_2$, $R^1OC(O)$—, $R^1(R^1O)CH$—, $R^1CH_2CH_2$—, $R^1CH_2$—, $PhC(O)CH_2$—, $CH_2$=CH—, $ClCH_2CH_2$—, $Ph_3C$—, $Ph_2(4$-pyridyl)C—, $Me_2N$—, HO—$CH_2$—, $R^1OCH_2$—, $(R^1)_3SiOCH_2$—, $(R^1O)_2CH$—, t-BuOC(O)$CH_2$—, $Me_2NCH_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl.

More preferably $B(R^5)_2$ represents a pinacol ester

The ninth aspect of the invention provides a method for the production of a compound of formula (VII)

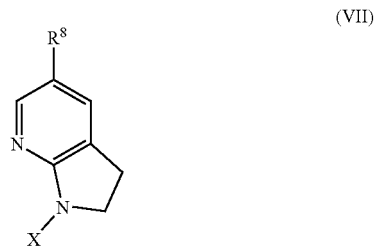

comprising a) reaction of a compound of formula (IV) with an electrophile, or b) reaction of a compound of formula (IV) with $R^6$-Z in the presence of a palladium catalyst or c) reaction of a compound of formula (V) with $R^6$-Z in the presence of a palladium catalyst or d) reacting a compound of formula (VI) with $R^7$-Z in the presence of a palladium catalyst;

wherein $R^8$ is an optionally substituted $C_{1-12}$ alkyl, $C_{2-12}$ alkenyl, $COR^9$ carbocyclyl or heterocyclyl group;

wherein $R^9$ is optionally subsituted alkyl, carbocyclyl or heterocyclyl; and wherein, each substitutable carbon atom in $R^8$ or $R^9$ is optionally and independently substituted by one or more of $C_{1-12}$ alkyl, $C_{2-12}$ alkenyl, carbocyclyl, or heterocyclyl, halogen, haloalkyl, $OR^{10}$, $SR^{10}$, $NO_2$, CN, $NR^{10}R^{10}$, $NR^{10}COR^{10}$, $NR^{10}CONR^{10}R^{10}$, $NR^{10}CO_2R^{10}$, $CO_2R^{10}$, $COR^{10}$, $CONR^{10}R^{10}$, $S(O)_2R^{10}$, $SONH_2$, $S(O)R^{10}$, $SO_2NR^{10}R^{10}$, $NR^{10}S(O)_2R^{10}$, wherein each $R^{10}$ may be the same or different and is as defined below; wherein the $C_{1-12}$ alkyl optionally incorporates one or two insertions selected from the group consisting of —O—, —C(O)—, —N($R^{10}$)—, —S(O)— and —S($O_2$)— and wherein the $C_{1-12}$ alkyl, carbocyclyl, or heterocyclyl group is optionally substituted by one or more of halogen, haloalkyl, $OR^{10}$, SR, $NO_2$, CN, $NR^{10}R^{10}$, $NR^{10}COR^{10}$, $NR^{10}CONR^{10}R^{10}$, $NR^{10}COR^{10}$, $NR^{10}CO_2R^{10}$, $CO_2R^{10}$, $COR^{10}$, $CONR^{10}_2$, $S(O)_2R^{10}$, $SONH_2$, $S(O)R^{10}$, or $NR^{10}S(O)_2R^{10}$;

each substitutable nitrogen atom in $R^8$ is optionally substituted by $R^{11}$, $COR^{10}$, $SO_2R^{10}$ or $CO_2R^{10}$, wherein each $R^{10}$ and $R^{11}$ may be the same or different and is as defined below;

the optionally substituted carbocyclyl or optionally substituted heterocyclyl group is optionally fused to an unsaturated, partially unsaturated or fully saturated five to seven membered ring containing zero to three heteroatoms, each saturated carbon in the optional fused ring is further optionally and independently substituted by =O, =S, =$NNHR^{10}$, $NNR^{10}R^{10}$, =N—$OR^{10}$, =$NNHCOR^{10}$, =$NNHCO_2R^{10}$, =$NNSO_2R^{10}$, or =$NR^{10}$, wherein each $R^{10}$ may be the same or different and is as defined below;

$R^{10}$ is hydrogen, $C_{1-12}$ alkyl or aryl, optionally substituted by one or more of $C_{1-4}$ alkyl, halogen, $C_{1-4}$ haloalkyl, $OR^{12}$, $SR^{12}$, $NO_2$, CN, $NR^{12}R^{12}$, $NR^{12}COR^{12}$, $NR^{12}CONR^{12}R^{12}$, $NR^{12}COR^{12}$, $NR^{12}CO_2R^{12}$, $CO_2R^{12}$, $COR^{12}$, $CONR^{12}_2$, $S(O)_2R^{12}$, $SONH_2$, $S(O)R^{12}$, $SO_2NR^{12}R^{12}$, $NR^{12}S(O)_2R^{12}$, wherein the $C_{1-12}$ alkyl group optionally incorporates one or two insertions selected from the group consisting of —O—, —N($R^{12}$)—, —S(O)— and —S($O_2$)—, wherein each $R^{12}$ may be the same or different and is as defined below;

$R^{11}$ is $C_{1-12}$ alkyl or aryl, optionally substituted by one or more of $C_{1-4}$ alkyl, halogen, $C_{1-4}$ haloalkyl, $OR^{12}$, $SR^{12}$, $NO_2$, CN, $NR^{12}R^{12}$, $NR^{12}COR^{12}$, $NR^{12}CONR^{12}R^{12}$, $NR^{12}COR^{12}$, $NR^{12}CO_2R^{12}$, $CO_2R^{12}$, $COR^{12}$, $CONR^{12}_2$, $S(O)_2R^{12}$, $SONH_2$, $S(O)R^{12}$, $SO_2NR^{12}R^{12}$, $NR^{12}S(O)_2R^{12}$, wherein the $C_{1-12}$ alkyl group optionally incorporates one or two insertions selected from the group consisting of —O—, —N($R^{12}$)—, —S(O)— and —S($O_2$)—, wherein each $R^{12}$ may be the same or different and is as defined below;

$R^{12}$ is hydrogen, $C_{1-4}$ alkyl, or $C_{1-4}$ haloalkyl;

wherein X is a amino-protecting group, preferably selected from $R^1S(O)_2$, $(R^1)_3Si$, $R^1C(O)$, $R^1OCH_2$, $R^1_2NSO_2$, $R^1OC(O)$—, $R^1(R^1O)CH$—, $R^1CH_2CH_2$—, $R^1CH_2$—, PhC(O)$CH_2$—, $CH_2$=CH—, $ClCH_2CH_2$—, $Ph_3C$—, $Ph_2$(4-pyridyl)C—, $Me_2N$—, HO—$CH_2$—, $R^1OCH_2$—, $(R^1)_3SiOCH_2$—, $(R^1O)_2CH$—, t-BuOC(O)$CH_2$—, $Me_2NCH_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl.

wherein $R^6$ and $R^7$ are independently selected from an optionally substituted $C_{1-12}$ alkyl, $C_{2-12}$ alkenyl, $COR^9$, carbocyclyl or heterocyclyl group and Z is a halogen preferably iodine, bromide or chlorine, or triflate.

In a preferred feature of the ninth aspect, $R^8$ is preferably substituted with one or more of alkyl (e.g. methyl, ethyl or propyl), haloalkyl (preferably $CF_3$), halogen (e.g. F, Cl or Br, preferably F), $OR^{13}$, $SR^{13}$, $SOR^{13}$, $N(R^{13})_2$, wherein $R^{13}$ is independently selected from hydrogen, $C_{1-4}$ alkyl or haloalkyl and is preferably phenyl or napthyl. When $R^8$ is phenyl it is preferably substituted in the 4-(para) position, by $NR^{14}R^{14}$, where $R^{14}$ is independently H or $C_{1-4}$ alkyl.

For the avoidance of doubt, when a group as defined above contains two or more radicals, e.g. the radical $R^{10}$, as for example in the groups $SO_2NR^{10}R^{10}$ and $NR^{10}COR^{10}$, the two or more radicals e.g. $R^{10}$ may be the same or different.

It will be appreciated that the reaction set out as option b) for the ninth aspect is a Stille reaction, which can be carried out according to Stille Angew. Chem., Int.ed, Engl. 1986, 25, 508; Mitchell Synthesis, 1992, 803, or Littke et al. J. Am. Chem. Soc. 2002, 124, 6343.

It will be appreciated that the reaction set out as option c) for the ninth aspect is a Hiyama reaction which can be carried out according to Hatanaka et al. J. Org. Chem. 1988, 53, 918, Hatanaka et al. Synlett, 1991, 845 or Tamao et al. Tetrahedron Lett. 1989, 30, 6051, or Denmark et al. Org. Lett. 2000, 2, 565, ibid. 2491.

The reaction set out as option d) for the ninth aspect is a Suzuki reaction which can be carried out according to Suzuki Pure Appl. Chem. 1991, 63, 419, or Littke J. Am. Chem. Soc. 2000, 122, 4020.

For the purposes of this invention, a compound of formula (IV) is preferably incubated with an electrophile such as a $C_{1-12}$ alkyl halide for example methyl iodide, DMF, $CO_2$, or a group $R^{10}$—C(O)H wherein $R^{10}$ is $C_{1-12}$ alkyl or $C_{6-12}$ aryl.

In a preferred feature of the ninth aspect, a compound of formula (VII) is produced by the palladium-catalysed coupling reaction between a stannane of formula (VIII) and a group $R^8$—Y wherein $R^8$ is a group as defined above and Y is a halogen,

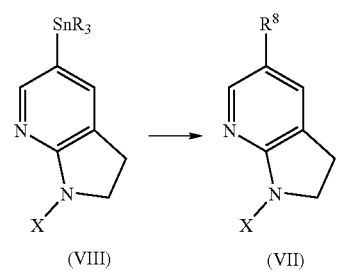

(VIII)          (VII)

Compound (VIII) is formed by the transmetallation of a compound of formula (I) or (IV) as described in the third aspect of the invention.

For the purposes of all aspects of this invention, alkyl relates to both straight chain and branched alkyl radicals of 1 to 12 carbon atoms, preferably 1 to 8 carbon atoms and most preferably 1 to 4 carbon atoms including but not limited to methyl, ethyl, n-propyl, isopropyl, n-butyl, sec-butyl, isobutyl, tert-butyl n-pentyl, n-hexyl, n-heptyl, n-octyl. In particular, alkyl relates to a group having 1, 2, 3, 4, 5, 6, 7, 8, 9, 10, 11 or 12 carbon atoms. The term alkyl also encompasses cycloalkyl radicals including but not limited to cyclopropyl, cyclobutyl, $CH_2$-cyclopropyl, $CH_2$-cyclobutyl, cyclopentyl or cyclohexyl. In particular, cycloalkyl relates to a group having 3, 4, 5, 6, 7, 8, 9, 10, 11 or 12 carbon atoms. Cycloalkyl groups may be optionally substituted or fused to one or more carbocyclyl or heterocyclyl group. Haloalkyl relates to an alkyl radical as defined above preferably having 1 to 8 carbon atoms, preferably 1 to 4 carbon atoms substituted with one or more halide atoms for example one or more of F, Cl, Br or I, such as $CH_2CH_2Br$, $CF_3$ or $CCl_3$.

The term "alkenyl" means a straight chain or branched alkylenyl radical of 2 to 12 carbon atoms, preferably 2 to 6 carbon atoms and most preferably 2 to 4 carbon atoms, and containing one or more carbon-carbon double bonds and includes but is not limited to ethylene, n-propyl-1-ene, n-propyl-2-ene, isopropylene, etc. In particular, alkenyl relates to a group having 2, 3, 4, 5, 6, 7, 8, 9, 10, 11 or 12 carbon atoms. The term "alkynyl" means a straight chain or branched alkynyl radical of 2 to 12 carbon atoms, preferably 2 to 6 carbon atoms and most preferably 2 to 4 carbon atoms, and containing one or more carbon-carbon triple bonds and includes but is not limited to ethynyl, 2-methylethynyl etc. In particular, alkynyl relates to a group having 2, 3, 4, 5, 6, 7, 8, 9, 10, 11 or 12 carbon atoms.

"Carbocyclyl" relates to a saturated, partly unsaturated or unsaturated 3-12 membered hydrocarbon ring preferably a 6-12 membered hydrocarbon ring, including cycloalkyl and aryl.

"Aryl" means an aromatic 3-12 membered hydrocarbon preferably a 6-12 membered hydrocarbon containing one ring or being fused to one or more saturated or unsaturated rings including but not limited to phenyl, napthyl, anthracenyl or phenanthracenyl.

"Heteroaryl" means an aromatic 3-12 membered aryl preferably a 6-12 membered aryl containing one or more heteroatoms selected from N, O or S and containing one ring or being fused to one or more saturated or unsaturated rings and;

"Heterocyclyl" means a 3-12 membered ring system preferably a 6-12 membered ring system containing one or more heteroatoms selected from N, O or S and includes heteroaryl. In particular the terms "carbocyclyl", "aryl", "heteroaryl" and "heterocyclyl" relate to a group having 3, 4, 5, 6, 7, 8, 9, 10, 11 or 12 carbon atoms.

The heterocyclyl system can contain one ring or may be fused to one or more saturated or unsaturated rings; the heterocyclyl can be fully saturated, partially saturated or unsaturated and includes but is not limited to heteroaryl and heterocarbocyclyl. Examples of carbocyclyl or heterocyclyl groups include but are not limited to cyclohexyl, phenyl, acridine, benzimidazole, benzofuran, benzothiophene, benzoxazole, benzothiazole, carbazole, cinnoline, dioxin, dioxane, dioxolane, dithiane, dithiazine, dithiazole, dithiolane, furan, imidazole, imidazoline, imidazolidine, indole, indoline, indolizine, indazole, isoindole, isoquinoline, isoxazole, isothiazole, morpholine, napthyridine, oxazole, oxadiazole, oxathiazole, oxathiazolidine, oxazine, oxadiazine, phenazine, phenothiazine, phenoxazine, phthalazine, piperazine, piperidine, pteridine, purine, pyran, pyrazine, pyrazole, pyrazoline, pyrazolidine, pyridazine, pyridine, pyrimidine, pyrrole, pyrrolidine, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, and trithiane.

For the purpose of the present invention, the term "fused" includes a polycyclic compound in which one ring contains one or more atoms preferably one, two or three atoms in common with one or more other ring.

Halogen means F, Cl, Br or I, preferably F.

Compounds of formula (VII) can be converted into alternative compounds of formula (VII) by conventional methods known in the art. In particular, a compound of formula (VII) may undergo oxidation, reduction, addition, elimination, substitution or transmetallation reactions in order to produce a further compound of formula (VII).

The compounds of formula (VII) can be aromatised to 5-substituted 7-azaindoles (IX) using methods known in the art, in particular $Mn(OAc)_3/AcOH$ or $MnO_2$.

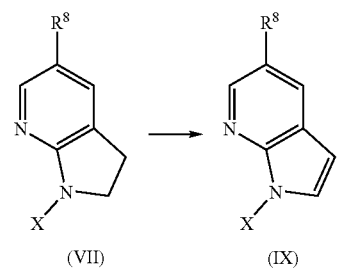

If the compounds of formula (IX) or derivatives thereof (for example compounds of formula (IX) wherein X is hydrogen) are produced for use in medicine, an alternative method to aromatise compounds of formula (VII) is preferred.

The tenth aspect of the invention provides a method of producing a compound of formula (XI) by the aromatisation of a compound of formula (X) with DDQ wherein efficient oxidation of derivative (X) with DDQ to afford (XI) is promoted by the presence of electron-donating N-silyl group at nitrogen in (X).

Scheme 4

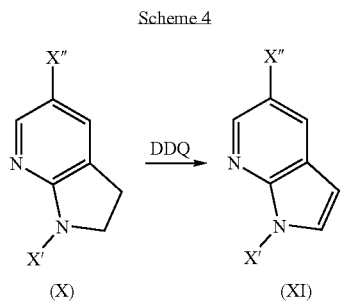

wherein X' is a silyl group $(R^1)_3Si$ $R^1$ is as defined in the first aspect

X" is Br or $R^8$ and $R^8$ is as defined in the ninth aspect

Preferably X' is t-butyldimethylsilyl (TBS), triisopropylsilyl (TIPS) or t-butyldimethylphenylsilyl (TBDPS).

As previously discussed, previous attempts in the art to rearomatise unprotected 7-azaindolines with DDQ resulted in undesirably low yields. The method set out in the tenth aspect of the inveniton utilises the presence of the electron-donating N-silyl group to promote efficient oxidation of (X) with DDQ.

This method allows the production of 5-substituted-7-azaindole moieties without the need for a high excess of oxidant and avoids the contamination of the product with heavy metal impurities (as can be seen for example with a $MnO_2$ or $Mn(OAc)_3/AcOH$ medicated oxidation).

Removal of the group X' can be carried out using method known in the art. Suitable methods for removing specific X' groups are set out in Greene and Wuts *Protective Groups in Organic Synthesis*, 3$^{rd}$ Edition, Wiley, New York, 1999. For example when X' is TBS, it can be removed by incubation with hydrochloric acid. Alternatively, when X' is $PhSO_2$, removal can be afforded with KOH in EtOH.

The eleventh aspect of the invention provides a compound of formula (XII)

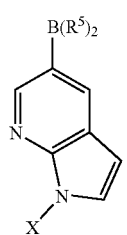

(XII)

wherein $R^5$ is OH or a group $OR^{20}$ wherein $R^{20}$ is $C_{1-6}$ alkyl or $C_{6-12}$ aryl and wherein two or more $R^{20}$ groups may together form a 4 to 7 membered ring, and wherein X is a amino-protecting group, preferably selected from $R^1S(O)_2$, $(R^1)_3Si$, $R^1C(O)$, $R^1OCH_2$, $R^1_2NSO_2$, $R^1OC(O)$—, $R^1(R^1O)CH$—, $R^1CH_2CH_2$—, $R^1CH_2$—, $PhC(O)CH_2$—, $CH_2$=CH—, $ClCH_2CH_2$—, $Ph_3C$—, $Ph_2$(4-pyridyl)C—, $Me_2N$—, HO—$CH_2$—, $R^1OCH_2$—, $(R^1)_3SiOCH_2$—, $(R^1O)_2CH$—, t-BuOC(O)$CH_2$—, $Me_2NCH_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl.

The twelfth aspect of the invention provides a method of producing a compound of formula (XII)

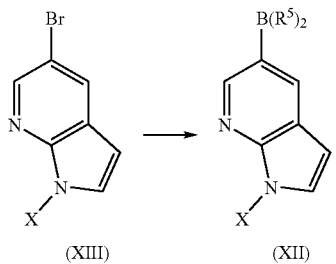

(XIII) (XII)

comprising incubating a compound of formula (XIII) with $(R^5)_3B$ and a base wherein $R^5$ is OH, $C_{1-6}$ alkoxy or $C_{6-12}$ aryloxy. Preferably, $(R^5)_3B$ is selected from $B(OR^{15})_3$ wherein $R^{15}$ is alkyl, cycloalkyl or two $R^{15}$ groups may together form a 4 to 7 membered ring wherein X is a amino-protecting group, preferably selected from $R^1S(O)_2$, $(R^1)_3Si$, $R^1C(O)$, $R^1OCH_2$, $R^1_2NSO_2$, $R^1OC(O)$—, $R^1(R^1O)CH$—, $R^1CH_2CH_2$—, $R^1CH_2$—, $PhC(O)CH_2$—, $CH_2$=CH—, $ClCH_2CH_2$—, $Ph_3C$—, $Ph_2$(4-pyridyl)C—, $Me_2N$—, HO—$CH_2$—, $R^1OCH_2$—, $(R^1)_3SiOCH_2$—, $(R^1O)_2CH$—, t-BuOC(O)$CH_2$—, $Me_2NCH_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl.

The thirteenth aspect of the invention provides a method for the production of a compound of formula (IX)

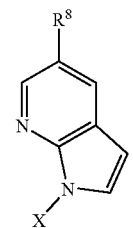

(IX)

comprising reacting a compound of formula (XII) with $R^7$-Z in the presence of a palladium catalyst.

wherein $R^8$ is an optionally substituted $C_{1-12}$ alkyl, $C_{2-12}$ alkenyl, $COR^9$ carbocyclyl or heterocyclyl group;

wherein $R^9$ is optionally substituted alkyl, carbocyclyl or heterocyclyl; and wherein, each substitutable carbon atom in $R^8$ or $R^9$ is optionally and independently substituted by one or more of $C_{1-12}$ alkyl, $C_{2-12}$ alkenyl, carbocyclyl, or heterocyclyl, halogen, haloalkyl, $OR^{10}$, $SR^{10}$, $NO_2$, CN, $NR^{10}R^{10}$, $NR^{10}COR^{10}$, $NR^{10}CONR^{10}R^{10}$, $NR^{10}COR^{10}$, $NR^{10}CO_2R^{10}$, $CO_2R^{10}$, $COR^{10}$, $CONR^{10}R^{10}$, $S(O)_2R^{10}$, $SONH_2$, $S(O)R^{10}$, $SO_2NR^{10}R^{10}$, $NR^{10}S(O)_2R^{10}$, wherein each $R^{10}$ may be the same or different and is as defined below; wherein the $C_{1-12}$ alkyl optionally incorporates one or two insertions selected from the group consisting of —O—, —C(O)—, —N($R^{10}$)—, —S(O)— and —S($O_2$)— and wherein the $C_{1-12}$ alkyl, carbocyclyl, or heterocyclyl group is optionally substituted by one or more of halogen, haloalkyl, $OR^{10}$, SR, $NO_2$, CN, $NR^{10}R^{10}$, $NR^{10}COR^{10}$, $NR^{10}CONR^{10}R^{10}$, $NR^{10}COR^{10}$, $NR^{10}CO_2R^{10}$, $CO_2R^{10}$, $COR^{10}$, $CONR^{10}_2$, $S(O)_2R^{10}$, $SONH_2$, $S(O)R^{10}$, or $NR^{10}S(O)_2R^{10}$;

each substitutable nitrogen atom in $R^8$ is optionally substituted by $R^{11}$, $COR^{10}$, $SO_2R^{10}$ or $CO_2R^{10}$, wherein each $R^{10}$ and $R^{11}$ may be the same or different and is as defined below;

the optionally substituted carbocyclyl or optionally substituted heterocyclyl group is optionally fused to an unsaturated, partially unsaturated or fully saturated five to seven membered ring containing zero to three heteroatoms, each saturated carbon in the optional fused ring is further optionally and independently substituted by =O, =S, =$NNHR^{10}$, $NNR^{10}R^{10}$, =N—$OR^{10}$, =$NNHCOR^{10}$, =$NNHCO_2R^{10}$, =$NNSO_2R^{10}$, or =$NR^{10}$, wherein each $R^{10}$ may be the same or different and is as defined below;

$R^{10}$ is hydrogen, $C_{1-12}$ alkyl or aryl, optionally substituted by one or more of $C_{1-4}$ alkyl, halogen, $C_{1-4}$ haloalkyl, $OR^{12}$, $SR^{12}$, $NO_2$, CN, $NR^{12}R^{12}$, $NR^{12}COR^{12}$, $NR^{12}CONR^{12}R^{12}$, $NR^{12}COR^{12}$, $NR^{12}CO_2R^{12}$, $CO_2R^{12}$, $COR^{12}$, $CONR^{12}_2$, $S(O)_2R^{12}$, $SONH_2$, $S(O)R^{12}$, $SO_2NR^{12}R^{12}$, $NR^{12}S(O)_2R^{12}$, wherein the $C_{1-12}$ alkyl group optionally incorporates one or two insertions selected from the group consisting of —O—, —N($R^{12}$)—, —S(O)— and —S($O_2$)—, wherein each $R^{12}$ may be the same or different and is as defined below;

$R^{11}$ is $C_{1-12}$ alkyl or aryl, optionally substituted by one or more of $C_{1-4}$ alkyl, halogen, $C_{1-4}$ haloalkyl, $OR^{12}$, $SR^{12}$, $NO_2$, CN, $NR^{12}R^{12}$, $NR^{12}COR^{12}$, $NR^{12}CONR^{12}R^{12}$, $NR^{12}COR^{12}$, $NR^{12}CO_2R^{12}$, $CO_2R^{12}$, $COR^{12}$, $CONR^{12}_2$, $S(O)_2R^{12}$, $SONH_2$, $S(O)R^{12}$, $SO_2NR^{12}R^{12}$, $NR^{12}S(O)_2R^{12}$, wherein the $C_{1-12}$ alkyl group optionally incorporates one or two insertions selected from the group consisting of —O—, —N(R$^{12}$)—, —S(O)— and —S(O$_2$)—, wherein each R$^{12}$ may be the same or different and is as defined below;

R$^{12}$ is hydrogen, C$_{1-4}$ alkyl, or C$_{1-4}$ haloalkyl;

wherein X is a amino-protecting group, preferably selected from R$^1$S(O)$_2$, (R$^1$)$_3$Si, R$^1$C(O), R$^1$OCH$_2$, R$^1{_2}$NSO$_2$, R$^1$OC(O)—, R$^1$(R$^1$O)CH—, R$^1$CH$_2$CH$_2$—, R$^1$CH$_2$—, PhC(O)CH$_2$—, CH$_2$=CH—, ClCH$_2$CH$_2$—, Ph$_3$C—, Ph$_2$(4-pyridyl)C—, Me$_2$N—, HO—CH$_2$—, R$^1$OCH$_2$—, (R$^1$)$_3$SiOCH$_2$—, (R$^1$O)$_2$CH—, t-BuOC(O)CH$_2$—, Me$_2$NCH$_2$— and tetrahydropyranylamine;

wherein R$^1$ is C$_{1-6}$ alkyl, C$_{3-12}$ cycloalkyl, C$_{1-6}$ haloalkyl, C$_{6-12}$ heterocyclyl or C$_{6-12}$ carbocyclyl; optionally substituted with one or more of C$_{1-6}$ alkyl, Si(R$^3$)$_3$, OR$^3$, NO$_2$, CO$_2$, CO$_2$R$^3$, halogen, haloalkyl, SR$^3$, CN, NR$^3$COR$^3$, COR$^{13}$CONR$^3$R$^3$, wherein R$^3$ is hydrogen or C$_{1-6}$ alkyl, preferably R$^1$ is methyl, ethyl, propyl, n-butyl, tert-butyl or phenyl.

wherein R$^7$ is independently selected from an optionally substituted C$_{1-12}$ alkyl, C$_{2-12}$ alkenyl, COR$^9$, carbocyclyl or heterocyclyl group and Z is a halogen or triflate preferably iodine, bromine or chlorine.

It will be appreciated that the reaction set out is a Suzuki reaction which can be carried out according to Suzuki *Pure Appl. Chem.*, 1991, 63, 419, or Littke *J. Am. Chem. Soc.* 2000, 122, 4020.

The fourteenth aspect of the invention provides a compound of formula (XIV)

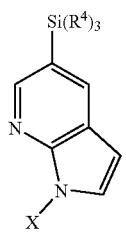

(XIV)

wherein R$^4$ is a C$_{1-6}$alkyl, OH, or an C$_{6-12}$ aryl group, X is an amino-protecting group, preferably selected from R$^1$S(O)$_2$, (R$^1$)$_3$Si, R$^1$C(O), R$^1$OCH$_2$, R$^1{_2}$NSO$_2$, R$^1$OC(O)—, R$^1$(R$^1$O)CH—, R$^1$CH$_2$CH$_2$—, R$^1$CH$_2$—, PhC(O)CH$_2$—, CH$_2$=CH—, ClCH$_2$CH$_2$—, Ph$_3$C—, Ph$_2$(4-pyridyl)C—, Me$_2$N—, HO—CH$_2$—, R$^1$OCH$_2$—, (R$^1$)$_3$SiOCH$_2$—, (R$^1$O)$_2$ CH—, t-BuOC(O)CH$_2$—, Me$_2$NCH$_2$— and tetrahydropyranylamine;

wherein R$^1$ is C$_{1-6}$ alkyl, C$_{3-12}$ cycloalkyl, C$_{1-6}$ haloalkyl, C$_{6-12}$ heterocyclyl or C$_{6-12}$ carbocyclyl; optionally substituted with one or more of C$_{1-6}$ alkyl, Si(R$^3$)$_3$, OR$^3$, NO$_2$, CO$_2$, CO$_2$R$^3$, halogen, haloalkyl, SR$^3$, CN, NR$^3$COR$^3$, COR$^{13}$CONR$^3$R$^3$, wherein R$^3$ is hydrogen or C$_{1-6}$ alkyl, preferably R$^1$ is methyl, ethyl, propyl, n-butyl, tert-butyl or phenyl.

The fifteenth aspect of the invention provides a method for the production of compound of formula (IX)

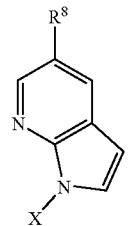

(IX)

comprising reacting a compound of formula (XII) with R$^7$-Z in the presence of a palladium catalyst wherein R$^8$ is an optionally substituted C$_{1-12}$ alkyl, C$_{2-12}$ alkenyl, COR$^9$ carbocyclyl or heterocyclyl group;

wherein R$^9$ is optionally substituted alkyl, carbocyclyl or heterocyclyl; and wherein, each substitutable carbon atom in R$^8$ or R$^9$ is optionally and independently substituted by one or more of C$_{1-12}$ alkyl, C$_{2-12}$ alkenyl, carbocyclyl, or heterocyclyl, halogen, haloalkyl, OR$^{10}$, SR$^{10}$, NO$_2$, CN, NR$^{10}$R$^{10}$, NR$^{10}$COR$^{10}$, NR$^{10}$CONR$^{10}$R$^{10}$, NR$^{10}$COR$^{10}$, NR$^{10}$CO$_2$R$^{10}$, CO$_2$R$^{10}$, COR$^{10}$, CONR$^{10}$R$^{10}$, S(O)$_2$R$^{10}$, SONH$_2$, S(O)R$^{10}$, SO$_2$NR$^{10}$R$^{10}$, NR$^{10}$S(O)$_2$R$^{10}$, wherein each R$^{10}$ may be the same or different and is as defined below; wherein: the C$_{1-12}$ alkyl optionally incorporates one or two insertions selected from the group consisting of —O—, —C(O)—, —N(R$^{10}$)—, —S(O)— and —S(O$_2$)— and wherein the C$_{1-12}$ alkyl, carbocyclyl, or heterocyclyl group is optionally substituted by one or more of halogen, haloalkyl, OR$^{10}$, SR, NO$_2$, CN, NR$^{10}$R$^{10}$, NR$^{10}$COR$^{10}$, NR$^{10}$CONR$^{10}$R$^{10}$, NR$^{10}$COR$^{10}$, NR$^{10}$CO$_2$R$^{10}$, CO$_2$R$^{10}$, COR$^{10}$, CONR$^{10}{_2}$, S(O)$_2$R$^{10}$, SONH$_2$, S(O)R$^{10}$, or NR$^{10}$S(O)$_2$R$^{10}$;

each substitutable nitrogen atom in R$^8$ is optionally substituted by R$^{11}$, COR$^{10}$, SO$_2$R$^{10}$ or CO$_2$R$^{10}$, wherein each R$^{10}$ and R$^{11}$ may be the same or different and is as defined below;

the optionally substituted carbocyclyl or optionally substituted heterocyclyl group is optionally fused to an unsaturated, partially unsaturated or fully saturated five to seven membered ring containing zero to three heteroatoms, each saturated carbon in the optional fused ring is further optionally and independently substituted by =O, =S, =NNHR$^{10}$, NNR$^{10}$R$^{10}$, =N—OR$^{10}$, =NNHCOR$^{10}$, =NNHCO$_2$R$^{10}$, =NNSO$_2$R$^{10}$, or =NR$^{10}$, wherein each R$^{10}$ may be the same or different and is as defined below;

R$^{10}$ is hydrogen, C$_{1-12}$ alkyl or aryl, optionally substituted by one or more of C$_{1-4}$ alkyl, halogen, C$_{1-4}$ haloalkyl, OR$^{12}$, SR$^{12}$, NO$_2$, CN, NR$^{12}$R$^{12}$, NR$^{12}$COR$^{12}$, NR$^{12}$CONR$^{12}$R$^{12}$, NR$^{12}$COR$^{12}$, NR$^{12}$CO$_2$R$^{12}$, CO$_2$R$^{12}$, COR$^{12}$, CONR$^{12}{_2}$, S(O)$_2$R$^{12}$, SONH$_2$, S(O)R$^{12}$, SO$_2$NR$^{12}$R$^{12}$, NR$^{12}$S(O)$_2$R$^{12}$, wherein the C$_{1-12}$ alkyl group optionally incorporates one or two insertions selected from the group consisting of —O—, —N(R$^{12}$)—, —S(O)— and —S(O$_2$)—, wherein each R$^{12}$ may be the same or different and is as defined below;

R$^{11}$ is C$_{1-12}$ alkyl or aryl, optionally substituted by one or more of C$_{1-4}$ alkyl, halogen, C$_{1-4}$ haloalkyl, OR$^{12}$, SR$^{12}$, NO$_2$, CN, NR$^{12}$R$^{12}$, NR$^{12}$COR$^{12}$, NR$^{12}$CONR$^{12}$R$^{12}$, NR$^{12}$COR$^{12}$, NR$^{12}$CO$_2$R$^{12}$, CO$_2$R$^{12}$, COR$^{12}$, CONR$^{12}{_2}$, S(O)$_2$R$^{12}$, SONH$_2$, S(O)R$^{12}$, SO$_2$NR$^{12}$R$^{12}$, NR$^{12}$S(O)$_2$R$^{12}$, wherein the C$_{1-12}$ alkyl group optionally incorporates one or two insertions selected from the group consisting of —O—, —N(R$^{12}$)—, —S(O)— and —S(O$_2$)—, wherein each R$^{12}$ may be the same or different and is as defined below;

$R^{12}$ is hydrogen, $C_{1-4}$ alkyl, or $C_{1-4}$ haloalkyl;

wherein X is a amino-protecting group, preferably selected from $R^1S(O)_2$, $(R^1)_3Si$, $R^1C(O)$, $R^1OCH_2$, $R^1_2NSO_2$, $R^1OC(O)$—, $R^1(R^1O)CH$—, $R^1CH_2CH_2$—, $R^1CH_2$—, $PhC(O)CH_2$—, $CH_2=CH$—, $ClCH_2CH_2$—, $Ph_3C$—, $Ph_2(4\text{-pyridyl})C$—, $Me_2N$—, $HO$—$CH_2$—, $R^1OCH_2$—, $(R^1)_3SiOCH_2$—, $(R^1O)_2CH$—, t-BuOC(O)CH$_2$—, Me$_2$NCH$_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl.

wherein $R^7$ is independently selected from an optionally substituted $C_{1-12}$ alkyl, $C_{2-12}$ alkenyl, $COR^9$, carbocyclyl or heterocyclyl group and Z is a halogen or triflate preferably iodide, bromide or chloride.

It will be appreciated that the reaction set out is a Hiyama reaction which can be carried out according to Hatanaka et al. *J. Org. Chem.* 1988, 53, 918, Hatanaka et al. *Synlett* 1991, 845 or Tamao et al. *Tetrahedron Lett.* 1989, 30, 6051, or Denmark et al. Org. Lett. 2000, 2, 565, ibid. 2491.

The sixteenth aspect of the invention provides a method of producing 7-azaindoline from 7-azaindole, comprising the reaction of 7-azaindole with a formic acid-triethylamine mixture in the presence of a palladium catalyst, followed by incubation with sodium hydroxide.

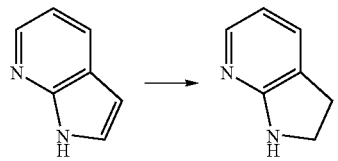

This method avoids using high pressure, gaseous hydrogen, avoids concomitant formation of overreduced products and occurs at relatively low temperature.

The seventeenth aspect provides a compound of formula (XV)

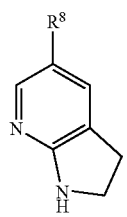

(XV)

wherein $R^8$ is as defined in the ninth aspect

In a preferred feature $R^8$ is substituted aryl, preferably substituted phenyl or optionally substituted five-membered heterocyclyl or aryl-C(O).

The eighteenth aspect provides a method for the production of a compound of formula (XV)

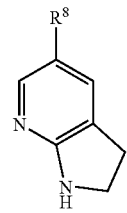

(XV)

comprising a) a reaction of a compound of formula (III) with $R^8$—$B(OR^{15})_2$ in the presence of a palladium catalyst

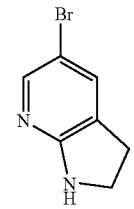

(III)

b) reacting a compound of formula (III) with $R^8$—$Sn(R^2)_3$ in the presence of a palladium catalyst c) reacting a compound of formula (III) with $R^8$—$Si(R^4)_3$ in the presence of a fluoride and a palladium catalyst;

wherein $R^8$ is as defined in the ninth aspect

In a preferred feature $R^8$ is substituted aryl, preferably substituted phenyl or optionally substituted five-membered heterocyclyl;

wherein $R^{15}$ is hydrogen, $C_{1-6}$ alkyl or $C_{6-12}$ aryl and wherein two or more $R^{15}$ groups may together form a 4 to 7 membered ring;

In a preferred feature $R^{15}$ is hydrogen, —$CMe_2CMe_2$—, methyl, ethyl.

wherein $R^2$ is as defined in the third aspect $R^4$ is as define d in the fifth aspect In a preferred feature $R^2$ is $C_{1-4}$ alkyl, most preferably methyl, ethyl, propyl and butyl.

For the avoidance of doubt, when a group as defined above contains two or more radicals, e.g. the radical $R^4$, as for example in $SiR^4R^4$, the two or more radicals e.g. $R^4$ may be the same or different.

It will be appreciated that the reaction set out in option a) for the eighteenth aspect is a Suzuki coupling reaction which can be carried out according to Suzuki *Pure Appl. Chem.* 1991, 63, 419; and Martin and Yang *Acta Chem. Scand.* 1993, 47, 221, or Littke J. Am. Chem. Soc. 2000, 122, 4020.

It will be appreciated that the reaction set out in option b) for the eighteenth aspect is a Stille coupling reaction which can be carried out according to Stille *Angew. Chem. Int. Ed.* 1986, 25, 508; Mitchell, *Synthesis* 1992, 803, or Littke et al. J. Am. Chem. Soc. 2002, 124, 6343.

It will be appreciated that the reaction set out in option c) for the eighteenth aspect is a Hiyama coupling reaction which can be carried out according to Hatanaka and Hiyama *J. Org. Chem.* 1988, 53, 918; Hatanaka and Hiyama *Synlett.* 1991, 845; Tamao et al. *Tetrahedron Lett.* 1989, 30, 6051, or Denmark et al. Org. Lett. 2000, 2, 565, ibid. 2491.

In a preferred feature of the eighteenth aspect a compound of formula (III) is incubated with an aryl boronic acid $R^8$—B(OH)$_2$, heteroaryl boronic acid $R^8$—B(OH)$_2$, aryltrialkyl stannane R⁸—Sn(R²)₃, or heteroaryltrialkylstannane R⁸—Sn(R²)₃ where R⁸ is as defined above and R² is C₁₋₄ alkyl.

Compound (III) is formed by bromination of 7-azaindoline according to methods known in the art.

The nineteenth aspect provides a method for the production of a compound of formula (VII)

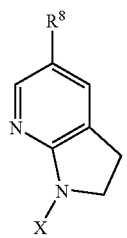

(VII)

comprising a) a reaction of a compound of formula (I) with R⁸—B(OR¹⁵)₂ in the presence of a palladium catalyst;

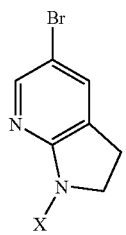

(I)

b) reacting a compound of formula (I) with R⁸—Sn(R²)₃ in the presence of a palladium catalyst or c) reacting a compound of formula (I) with R⁸—Si(R⁴)₃ in the presence of a fluoride and a palladium catalyst;

wherein R⁸ is as defined in the ninth aspect

In a preferred feature R⁸ is substituted aryl, preferably substituted phenyl or optionally substituted five-membered heterocyclyl;

wherein X is an amino-protecting group as defined in the first aspect, preferably selected from R¹S(O)₂, (R¹)₃Si, R¹C(O), R¹OCH₂, R¹₂NSO₂, R¹OC(O)—, R¹(R¹O)CH—, R¹CH₂CH₂—, R¹CH₂—, PhC(O)CH₂—, CH₂=CH—, ClCH₂CH₂—, Ph₃C—, Ph₂(4-pyridyl)C—, Me₂N—, HO—CH₂—, R¹OCH₂—, (R¹)₃SiOCH₂—, (R¹O)₂CH—, t-BuOC(O)CH₂—, Me₂NCH₂— and tetrahydropyranylamine;

wherein R¹ is C₁₋₆ alkyl, C₃₋₁₂ cycloalkyl, C₁₋₆ haloalkyl, C₆₋₁₂ heterocyclyl or C₆₋₁₂ carbocyclyl; optionally substituted with one or more of C₁₋₆ alkyl, Si(R³)₃, OR³, NO₂, CO₂, CO₂R³, halogen, haloalkyl, SR³, CN, NR³COR³, COR¹³CONR³R³, wherein R³ is hydrogen or C₁₋₆ alkyl, preferably R¹ is methyl, ethyl, propyl, n-butyl, tert-butyl or phenyl.

wherein R¹⁵ is hydrogen, C₁₋₆ alkyl or C₆₋₁₂ aryl and wherein two or more R¹⁵ groups may together form a 4 to 7 membered ring;

In a preferred feature R¹⁵ is hydrogen, —CMe₂CMe₂—, methyl, ethyl.

wherein R² is as defined in the third aspect

In a preferred feature R² is C₁₋₄ alkyl, most preferably methyl, ethyl, propyl and butyl.

R⁴ is as defined in the fifth aspect

For the avoidance of doubt, when a group as defined above contains two or more radicals, e.g. the radical R¹, as for example in NR¹R¹, the two or more radicals e.g. R¹ may be the same or different.

It will be appreciated that the reaction set out in option a) for the nineteenth aspect is a Suzuki coupling reaction which can be carried out according to Suzuki *Pure Appl. Chem.* 1991, 63, 419; and Martin and Yang *Acta Chem. Scand.* 1993, 47, 221, or Littke *J. Am. Chem. Soc.* 2000, 122, 4020.

It will be appreciated that the reaction set out in option b) for the nineteenth aspect is a Stille coupling reaction which can be carried out according to Stille *Angew. Chem. Int. Ed.* 1986 25, 508; Mitchell, *Synthesis* 1992, 803, or Littke et al. *J. Am. Chem. Soc.* 2002, 124, 6343.

It will be appreciated that the reaction set out in option c) for the nineteenth aspect is a Hiyama coupling reaction which can be carried out according to Hatanaka and Hiyama *J. Org. Chem.* 1988, 53, 918; Hatanaka and Hiyama Synlett. 1991, 845; Tamao et al. *Tetrahedron Lett.* 1989, 30, 6051, or Denmark et al. *Org. Lett.* 2000, 2, 565, ibid. 2491.

In a preferred feature of the nineteenth aspect a compound of formula (I) is incubated with an aryl boronic acid R⁸—B(OH)₂, heteroaryl boronic acid R⁸—B(OH)₂, aryltrialkyl stannane R⁸—Sn(R²)₃, or heteroaryltrialkylstannane R⁸—Sn(R²)₃ where R⁸ is as defined above and R² is C₁₋₄ alkyl.

The twentieth aspect provides a compound of formula (XIII)

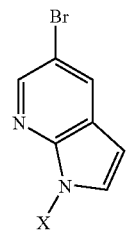

(XIII)

wherein X is an amino-protecting group as defined in the first aspect, preferably selected from R¹S(O)₂, (R¹)₃Si, R¹C(O), R¹OCH₂, R¹₂NSO₂, R¹OC(O)—, R¹(R¹O)CH—, R¹CH₂CH₂—, R¹CH₂—, PhC(O)CH₂—, CH₂=CH—, ClCH₂CH₂—, Ph₃C—, Ph₂(4-pyridyl)C—, Me₂N—, HO—CH₂—, R¹OCH₂—, (R¹)₃SiOCH₂—, (R¹O)₂CH—, t-BuOC(O)CH₂—, Me₂NCH₂— and tetrahydropyranylamine;

wherein R¹ is C₁₋₆ alkyl, C₃₋₁₂ cycloalkyl, C₁₋₆ haloalkyl, C₆₋₁₂ heterocyclyl or C₆₋₁₂ carbocyclyl; optionally substituted with one or more of C₁₋₆ alkyl, Si(R³)₃, OR³, NO₂, CO₂, CO₂R³, halogen, haloalkyl, SR³, CN, NR³COR³, COR¹³CONR³R³, wherein R³ is hydrogen or C₁₋₆ alkyl, preferably R¹ is methyl, ethyl, propyl, n-butyl, tert-butyl or phenyl.

The twenty first aspect provides a method for the production of a compound of formula (XVI)

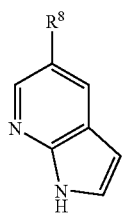

(XVI)

comprising a) a reaction of a compound of formula (XVII) with $R^8$—$B(OR^{15})_2$ in the presence of a palladium catalyst; or

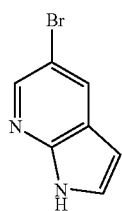

(XVII)

b) reacting a compound of formula (XVII) with $R^8$—$Sn(R^2)_3$ in the presence of a palladium catalyst c) reacting a compound of formula (XVII) with $R^8$—$Si(R^4)_3$ in the presence of a fluoride and a palladium catalyst;

wherein $R^8$ is as defined in the ninth aspect

In a preferred feature $R^8$ is substituted aryl, preferably substituted phenyl or optionally substituted five-membered heterocyclyl;

wherein $R^2$ is as defined in the third aspect

In a preferred feature $R^2$ is $C_{1-4}$ alkyl, most preferably methyl, ethyl, propyl and butyl.

wherein $R^4$ is as defined in the fifth aspect wherein $R^{15}$ is as defined in the seventh aspect In a preferred feature $R^{15}$ is hydrogen, —$CMe_2CMe_2$—, methyl, ethyl.

For the avoidance of doubt, when a group as defined above contains two or more radicals, e.g. the radical $R^2$, as for example in $SnR^2R^2$, the two or more radicals e.g. $R^2$ may be the same or different.

It will be appreciated that the reaction set out in option a) for the twenty first aspect is a Suzuki coupling reaction which can be carried out according to Suzuki *Pure Appl. Chem.* 1991, 63, 419; and Martin and Yang *Acta Chem. Scand.* 1993, 47, 221, or Littke *J. Am. Chem. Soc.* 2000, 122, 4020.

It will be appreciated that the reaction set out in option b) for the twenty first aspect is a Stille coupling reaction which can be carried out according to Stille *Angew. Chem. Int. Ed.* 1986, 25, 508; Mitchell, *Synthesis* 1992, 803, or Littke et al. *J. Am. Chem. Soc.* 2002, 124, 6343.

It will be appreciated that the reaction set out in option c) for the twenty first aspect is a Hiyama coupling reaction which can be carried out according to Hatanaka and Hiyama *J. Org. Chem.* 1988, 53, 918; Hatanaka and Hiyama *Synlett.* 1991, 845; Tamao et al. *Tetrahedron Lett.* 1989, 30, 6051, or Denmark et al. Org. Lett. 2000, 2, 565, ibid. 2491.

In a preferred feature of the twenty first aspect a compound of formula (I) is incubated with an aryl boronic acid $R^8$—$B(OH)_2$, heteroaryl boronic acid $R^8$—$B(OH)_2$, aryltrialkyl stannane $R^8$—$Sn(R^2)_3$, or heteroaryltrialkylstannane $R^8$—$Sn(R^2)_3$ where $R^8$ is as defined above and $R^2$ is $C_{1-4}$ alkyl.

The twenty-second aspect provides a method for the production of a compound of formula (IX)

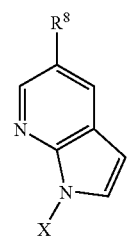

(IX)

comprising a) a reaction of a compound of formula (XIII) with $R^8$—$B(OR^{15})_2$ in the presence of a palladium catalyst; or

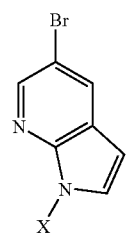

(XIII)

b) reacting a compound of formula (XIII) with $R^8$—$Sn(R^2)_3$ in the presence of a palladium catalyst c) reacting a compound of formula (XIII) with $R^8$—$Si(R^4)_3$ in the presence of a fluoride and a palladium catalyst;

wherein $R^2$ is as defined in the third aspect wherein $R^4$ is as defined in the fifth aspect wherein $R^8$ is as defined in the ninth aspect In a preferred feature $R^8$ is substituted aryl, preferably substituted phenyl or optionally substituted five-membered heterocyclyl;

wherein X is an amino-protecting group as defined in the first aspect of the invention, preferably selected from $R^1S(O)_2$, $(R^1)_3Si$, $R^1C(O)$, $R^1OCH_2$, $R^1{}_2NSO_2$, $R^1OC(O)$—, $R^1(R^1O)CH$—, $R^1CH_2CH_2$—, $R^1CH_2$—, $PhC(O)CH_2$—, $CH_2$=CH—, $ClCH_2CH_2$—, $Ph_3C$—, $Ph_2$(4-pyridyl)C—, $Me_2N$—, HO—$CH_2$—, $R^1OCH_2$—, $(R^1)_3SiOCH_2$—, $(R^1O)_2CH$—, t-BuOC(O)$CH_2$—, $Me_2NCH_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl.

wherein $R^{15}$ is as defined in the seventh aspect

In a preferred feature $R^{15}$ is hydrogen, —$CMe_2CMe_2$—, methyl, ethyl.

In a preferred feature $R^2$ is $C_{1-4}$ alkyl, most preferably methyl, ethyl, propyl and butyl.

$R^4$ is hydrogen, $C_{1-4}$ alkyl, or $C_{1-4}$ haloalkyl;

For the avoidance of doubt, when a group as defined above contains two or more radicals, e.g. the radical $R^2$, as for example in $SnR^2R^2$, the two or more radicals e.g. $R^2$ may be the same or different.

It will be appreciated that the reaction set out in option a) for the twenty-second aspect is a Suzuki coupling reaction which can be carried out according to Suzuki *Pure Appl. Chem.* 1991, 63, 419; and Martin and Yang *Acta Chem. Scand.* 1993, 47, 221, or Littke J. Am. Chem. Soc. 2000, 122, 4020.

It will be appreciated that the reaction set out in option b) for the twenty-second aspect is a Stille coupling reaction which can be carried out according to Stille *Angew. Chem. Int. Ed.* 1986, 25, 508; Mitchell, *Synthesis* 1992, 803, or Littke et al. J. Am. Chem. Soc. 2002, 124, 6343.

It will be appreciated that the reaction set out in option c) for the twenty-second aspect is a Hiyama coupling reaction which can be carried out according to Hatanaka and Hiyama *J. Org. Chem.* 1988, 53, 918; Hatanaka and Hiyama *Synlett.* 1991, 845; Tamao et al. *Tetrahedron Lett.* 1989, 30, 6051, or Denmark et al. Org. Lett. 2000, 2, 565, ibid. 2491.

In a preferred feature of the twenty-second aspect a compound of formula (I) is incubated with an aryl boronic acid $R^8$—$B(OH)_2$, heteroaryl boronic acid $R^8$—$B(OH)_2$, aryltrialkyl stannane $R^8$—$Sn(R^2)_3$, or heteroaryltrialkylstannane $R^8$—$Sn(R^2)_3$ where $R^8$ is as defined above and $R^2$ is $C_{1-4}$ alkyl.

The twenty third aspect of the invention provides an alternative method for the production of a compound of formula (IX)

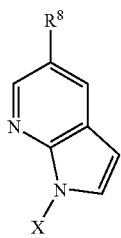
(IX)

comprising a reaction of a compound of formula (XVIII) with $R^6$-Z in the presence of a palladium catalyst

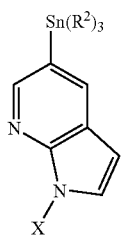
(XVIII)

wherein $R^2$ is as defined in the third aspect
wherein $R^6$ and $R^8$ are as defined in the ninth aspect
wherein Z is defined in the fifth aspect
wherein X is an amino-protecting group as defined in the first aspect, preferably selected from $R^1S(O)_2$, $(R^1)_3Si$, $R^1C(O)$, $R^1OCH_2$, $R^1{}_2NSO_2$, $R^1OC(O)$—, $R^1(R^1O)CH$—, $R^1CH_2CH_2$—, $R^1CH_2$—, $PhC(O)CH_2$—, $CH_2=CH$—, $ClCH_2CH_2$—, $Ph_3C$—, $Ph_2(4\text{-pyridyl})C$—, $Me_2N$—, $HO$—$CH_2$—, $R^1OCH_2$—, $(R^1)_3SiOCH_2$—, $(R^1O)_2CH$—, t-BuOC(O)$CH_2$—, $Me_2NCH_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl.

It will be appreciated that the reaction set out in the twenty third aspect is a Stille coupling reaction which can be carried out according to Stille *Angew. Chem. Int. Ed.* 1986, 25, 508; Mitchell, *Synthesis* 1992, 803, or Littke et al. J. Am. Chem. Soc. 2002, 124, 6343.

The twenty fourth aspect provides a compound of formula (XVIII)

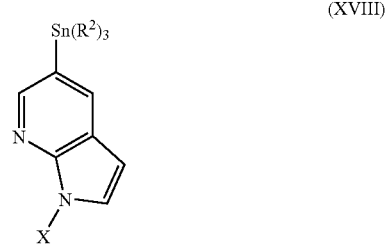
(XVIII)

wherein $R^2$ is as defined in the third aspect
wherein X is an amino-protecting group as defined in the first aspect, preferably selected from $R^1S(O)_2$, $(R^1)_3Si$, $R^1C(O)$, $R^1OCH_2$, $R^1{}_2NSO_2$, $R^1OC(O)$—, $R^1(R^1O)CH$—, $R^1CH_2CH_2$—, $R^1CH_2$—, $PhC(O)CH_2$—, $CH_2=CH$—, $ClCH_2CH_2$—, $Ph_3C$—, $Ph_2(4\text{-pyridyl})C$—, $Me_2N$—, $HO$—$CH_2$—, $R^1OCH_2$—, $(R^1)_3SiOCH_2$—, $(R^1O)_2CH$—, t-BuOC(O)$CH_2$—, $Me_2NCH_2$— and tetrahydropyranylamine;

wherein $R^1$ is $C_{1-6}$ alkyl, $C_{3-12}$ cycloalkyl, $C_{1-6}$ haloalkyl, $C_{6-12}$ heterocyclyl or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, preferably $R^1$ is methyl, ethyl, propyl, n-butyl, tert-butyl or phenyl.

The twenty fifth aspect of the invention provides a method of producing a compound of formula (XVIII)

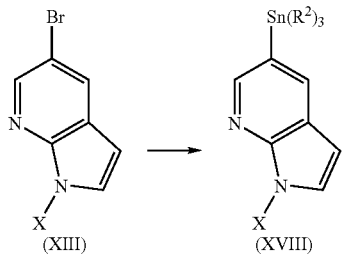

comprising incubating a compound of formula (XIII) with a base followed by addition of $(R^2)_3Sn$—W
wherein $R^2$ and W are as defined in the third aspect
wherein X is an amino-protecting group as defined in the first aspect, preferably selected from $R^1S(O)_2$, $(R^1)_3Si$, $R^1C(O)$, $R^1OCH_2$, $R^1{}_2NSO_2$, $R^1OC(O)$—, $R^1(R^1O)CH$—, $R^1CH_2CH_2$—, $R^1CH_2$—, $PhC(O)CH_2$—, $CH_2=CH$—, $ClCH_2CH_2$—, $Ph_3C$—, $Ph_2(4\text{-pyridyl})C$—, $Me_2N$—, HO—CH$_2$—, R$^1$OCH$_2$—, (R$^1$)$_3$SiOCH$_2$—, (R$^1$O)$_2$CH—, t-BuOC(O)CH$_2$—, Me$_2$NCH$_2$— and tetrahydropyranylamine;

wherein R$^1$ is C$_{1-6}$ alkyl, C$_{3-12}$ cycloalkyl, C$_{1-6}$ haloalkyl, C$_{6-12}$ heterocyclyl or C$_{6-12}$ carbocyclyl; optionally substituted with one or more of C$_{1-6}$ alkyl, Si(R$^3$)$_3$, OR$^3$, NO$_2$, CO$_2$, CO$_2$R$^3$, halogen, haloalkyl, SR$^3$, CN, NR$^3$COR$^3$, COR$^{13}$CONR$^3$R$^3$, wherein R$^3$ is hydrogen or C$_{1-6}$ alkyl, preferably R$^1$ is methyl, ethyl, propyl, n-butyl, tert-butyl or phenyl.

The twenty sixth aspect provides a compound of formula (VIIa)

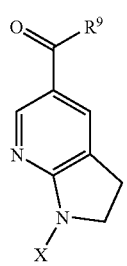

(VIIa)

wherein R$^9$ is as defined in the ninth aspect wherein X is an amino-protecting group as defined in the first aspect, preferably selected from R$^1$S(O)$_2$, (R$^1$)$_3$Si, R$^1$C(O), R$^1$OCH$_2$, R$^1$$_2$NSO$_2$, R$^1$OC(O)—, R$^1$(R$^1$O)CH—, R$^1$CH$_2$CH$_2$—, R$^1$CH$_2$—, PhC(O)CH$_2$—, CH$_2$=CH—, ClCH$_2$CH$_2$—, Ph$_3$C—, Ph$_2$(4-pyridyl)C—, Me$_2$N—, HO—CH$_2$—, R$^1$OCH$_2$—, (R$^1$)$_3$SiOCH$_2$—, (R$^1$O)$_2$CH—, t-BuOC(O)CH$_2$—, Me$_2$NCH$_2$— and tetrahydropyranylamine;

wherein R$^1$ is C$_{1-6}$ alkyl, C$_{3-12}$ cycloalkyl, C$_{1-6}$ haloalkyl, C$_{6-12}$ heterocyclyl or C$_{6-12}$ carbocyclyl; optionally substituted with one or more of C$_{1-6}$ alkyl, Si(R$^3$)$_3$, OR$^3$, NO$_2$, CO$_2$, CO$_2$R$^3$, halogen, haloalkyl, SR$^3$, CN, NR$^3$COR$^3$, COR$^{13}$CONR$^3$R$^3$, wherein R$^3$ is hydrogen or C$_{1-6}$ alkyl, preferably R$^1$ is methyl, ethyl, propyl, n-butyl, tert-butyl or phenyl.

The twenty seventh aspect provides a compound of formula (IXa)

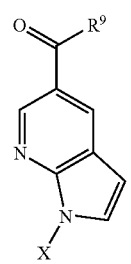

(IXa)

wherein R$^9$ is as defined in the ninth aspect wherein X is an amino-protecting group as defined in the first aspect, preferably selected from R$^1$S(O)$_2$, (R$^1$)$_3$Si, R$^1$C(O), R$^1$OCH$_2$, R$^1$$_2$NSO$_2$, R$^1$OC(O)—, R$^1$(R$^1$O)CH—, R$^1$CH$_2$CH$_2$—, R$^1$CH$_2$—, PhC(O)CH$_2$—, CH$_2$=CH—, ClCH$_2$CH$_2$—, Ph$_3$C—, Ph$_2$(4-pyridyl)C—, Me$_2$N—, HO—CH$_2$—, R$^1$OCH$_2$—, (R$^1$)$_3$SiOCH$_2$—, (R$^1$O)$_2$CH—, t-BuOC(O)CH$_2$—, Me$_2$NCH$_2$— and tetrahydropyranylamine;

wherein R$^1$ is C$_{1-6}$ alkyl, C$_{3-12}$ cycloalkyl, C$_{1-6}$ haloalkyl, C$_{6-12}$ heterocyclyl or C$_{6-12}$ carbocyclyl; optionally substituted with one or more of C$_{1-6}$ alkyl, Si(R$^3$)$_3$, OR$^3$, NO$_2$, CO$_2$, CO$_2$R$^3$, halogen, haloalkyl, SR$^3$, CN, NR$^3$COR$^3$, COR$^{13}$CONR$^3$R$^3$, wherein R$^3$ is hydrogen or C$_{1-6}$ alkyl, preferably R$^1$ is methyl, ethyl, propyl, n-butyl, tert-butyl or phenyl.

The twenty eighth aspect provides a compound of formula (XVIa)

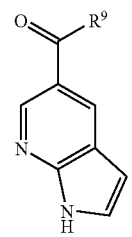

(XVIa)

wherein R$^9$ is as defined in the ninth aspect

The present invention encompasses one or more compounds as defined in the first, fourth, fifth, sixth, seventh, ninth, twelfth, thirteenth, fourteenth, fifteenth, sixteenth, eighteenth, twentieth, twenty fourth, twenty sixth, twenty seventh and twenty eighth aspects of the invention and as set out below;

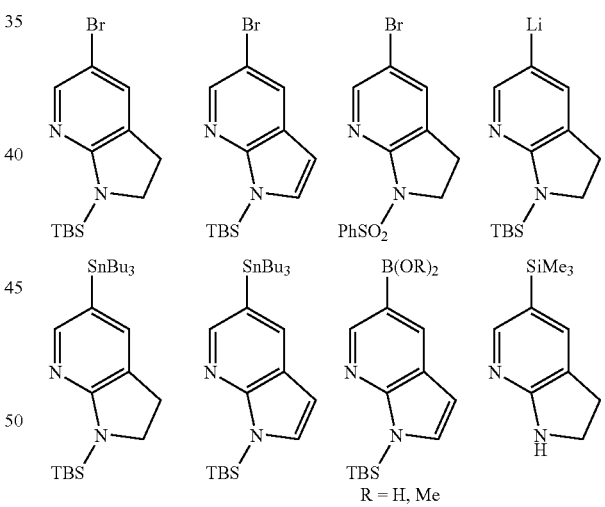

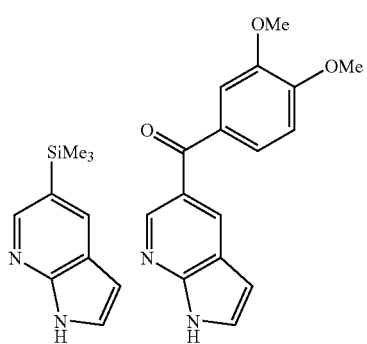

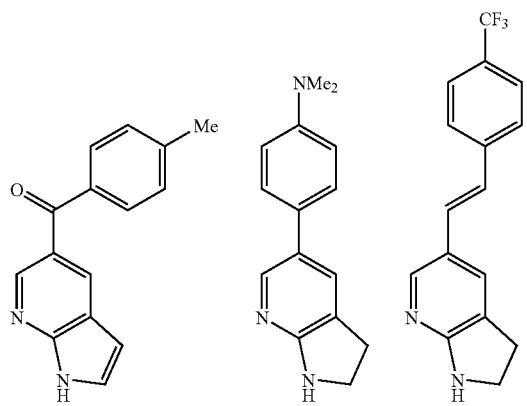

All features of each of the aspects apply to all other aspects mutatis mutandis.

The invention will now be illustrated by reference to one or more of the following non-limiting examples.

EXPERIMENTAL

Synthesis of N-protected 5-bromo-7-azaindolines 4 and 6

2,3-Dihydro-1H-pyrrolo[2,3-b]pyridine (2)

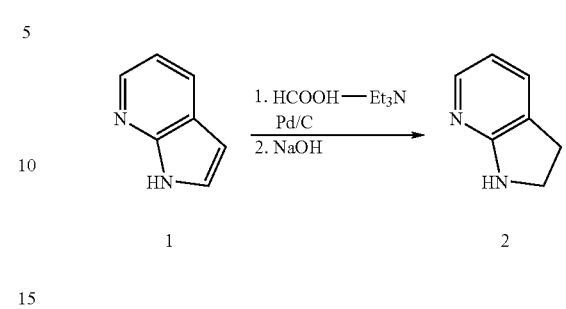

98% Formic acid (37.5 mL, 0.97 mol) was added to a stirred and cooled (ice bath) neat $Et_3N$ (150 mL, 1.08 mol). A two-phase system, which was formed, was then added to a mixture of 7-azaindole (50.0 g, 0.424 mol), formic acid (750 mL), and 10% palladium on activated carbon (26.75 g, Degussa type), and stirred at 80° C. for 4 d. The mixture was cooled to r.t., the catalyst was filtered off and washed with formic acid (100 mL). The filtrate and washings were combined and concentrated in vacuum. The residual liquid was cooled (ice bath) and basified to pH 13 by slow addition of 50% aqueous NaOH (total of about 500 mL). Then, the mixture was refluxed for 2 h until TLC showed completion. Ice was added in amount sufficient to lower the temperature of the mixture to 20° C. The two-phase system was then extracted with AcOEt (5×500 mL). Combined extracts were washed

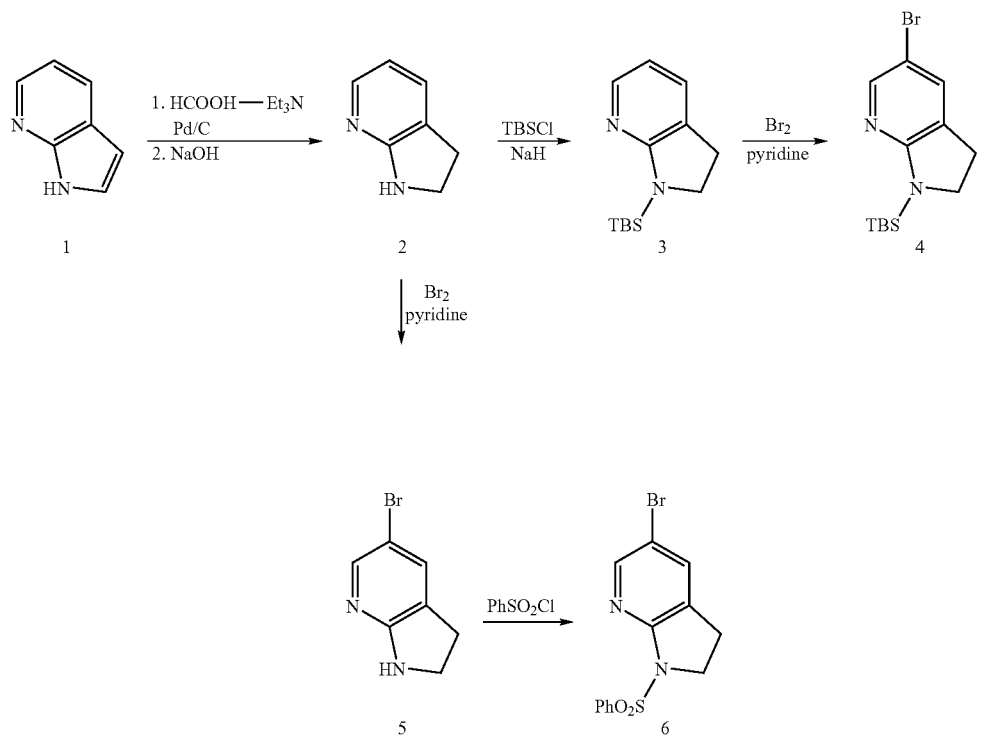

with brine, dried MgSO$_4$, and concentrated in vacuum. The residual brown solid was separated by means of SGC with AcOEt:MeOH as eluent to afford recovered 1 (12.57 g, 25%) and desired 2 (36.05 g, 71%). $^1$H NMR (400 MHz, CDCl$_3$) δ 3.05 (t, J=8.4 Hz, 2H), 3.60 (t, J=8.4 Hz, 2H), 4.52 (bs, 1H), 6.49 (dd, J=7.0, 5.3 Hz, 1H), 7.23 (dq, J=7.0, 1.3 Hz, 1H), 7.81 (ddt, J=5.3, 1.3, 1.1 Hz, 1H).

1-(tert-Butyl-dimethyl-silanyl)-2,3-dihydro-1H-pyrrolo[2,3-b]pyridine (3)

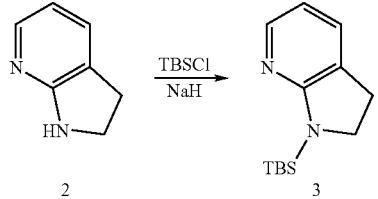

To a stirred and cooled (0° C.) solution of 7-azaindoline 2 (6.6 g, 54.9 mmol) in N,N-dimethylacetamide (18.5 mL) was added a 60% dispersion of sodium hydride in mineral oil (3.3 g, 82.4 mmol) portionwise. The mixture was stirred for 30 min and a solution of TBSCl (12.41 g, 82.4 mmol) in N,N-dimethylacetamide (25.1 mL) was added dropwise. The mixture was allowed to warm slowly to r.t. Following a further 18 h stirring the mixture was partitioned between AcOEt and saturated brine. The aqueous layer was extracted with AcOEt (2×). The combined organic solutions were washed with brine, dried (MgSO$_4$), filtered and concentrated. The residue was purified by silicagel chromatography (SGC) using hexane:AcOEt as eluent (in gradient) to afford the desired 3 (8.15 g, 63%) as a pale yellow oil. $^1$H NMR (400 MHz; CDCl$_3$) δ 0.33 (s, 6H), 0.97 (s, 9H), 2.99 (t, J=9.1 Hz, 2H), 3.65 (t, J=9.1 Hz, 2H), 6.38 (d, J=5.2 Hz, 1H), 7.14 (d, J=1.7 Hz, 1H), 7.79 (dd, J=1.7, 5.2 Hz, 1H).

5-Bromo-1-(tert-butyl-dimethyl-silanyl)-2,3-dihydro-1H-pyrrolo[2,3-b]pyridine (4)

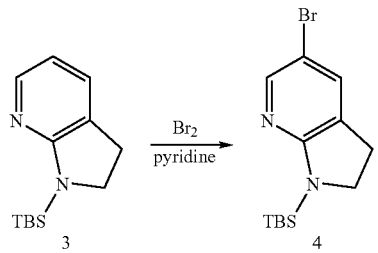

To a stirred and cooled (0° C.) solution of the azaindoline 3 (1.1 g, 4.7 mmol) in CH$_2$Cl$_2$ (25 mL) and pyridine (0.46 mL, 5.6 mmol) was added dropwise a solution of bromine (0.24 mL, 4.7 mmol) in CH$_2$Cl$_2$ (15 mL) over a period of 13 min. After a further 20 min stirring the mixture was diluted with a NaHCO$_3$—Na$_2$S$_2$O$_3$ (1:1 v/v) solution and stirred vigorously for 50 min. The resulting mixture was partitioned and the aqueous layer extracted with CH$_2$Cl$_2$ (3×). The combined organic extracts were dried (MgSO$_4$), filtered and concentrated. The residue was purified by SGC with hexane:AcOEt as eluent (in gradient up to 1.3% AcOEt) to afford the bromo derivative 4 (1.13 g, 77%) as a pale yellow oil. $^1$H NMR (400 MHz; CDCl$_3$) δ 0.31 (s, 6H), 0.95 (s, 9H), 2.99 (t, J=9.1 Hz, 2H), 3.67 (t, J=9.1 Hz, 2H), 7.20 (m, 1H), 7.79 (m, 1H).

5-Bromo-2,3-dihydro-1H-pyrrolo[2,3-b]pyridine (5)

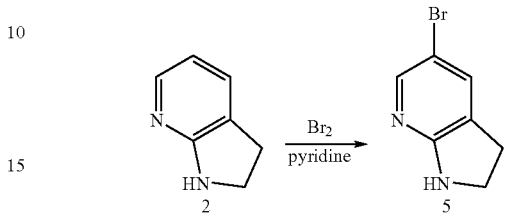

A solution of Br$_2$ (18.1 mL, 56.2 g, 0.351 mol) in dry CH$_2$Cl$_2$ (250 mL) was added dropwise over a period of 1 h 45 min to a stirred and cooled (−5° C.) solution of 2 (42.22 g, 0.351 mol) in dry CH$_2$Cl$_2$ (410 mL)-pyridine (40 mL). The yellow suspension was stirred at 0° C. for 45 min and poured into a mixture of saturated aqueous NaHCO$_3$ (800 mL) and saturated aqueous Na$_2$S$_2$O$_3$ (100 mL). Methanol (10 mL) was added and the lower organic layer was separated and dried over MgSO$_4$. The aqueous layer was extracted with AcOEt:MeOH=99:1 (7×1000 mL). These extracts were also dried with MgSO$_4$. The organic solutions were combined and concentrated to afford 5 (59.17 g, 85%), which was used in the next step without further purification. $^1$H NMR (400 MHz, CDCl$_3$) δ 3.07 (tt, J=8.4, 1.1 Hz, 2H), 3.64 (t, J=8.4 Hz, 2H), 4.47 (bs, 1H), 7.31 (m, 1H), 7.85 (dt, J=2.1, 0.9 Hz, 1H).

1-Benzenesulfonyl-5-bromo-2,3-dihydro-1H-pyrrolo[2,3-b]pyridine (6)

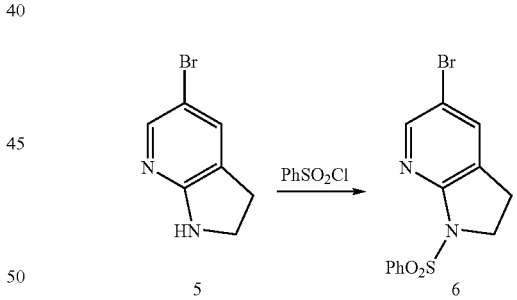

To a 0° C. stirred solution of 5-bromo-azaindoline 5 (150 mg, 0.75 mmol) in N,N-dimethylacetamide (7 mL) was added in one portion 60% dispersion of NaH in mineral oil (38 mg, 0.94 mmol). After 0.5 h benzenesulfonyl chloride (0.12 mL, 0.94 mmol) in N,N-dimethylacetamide (1 mL) was added dropwise, and the mixture allowed to slowly warm to r.t. After 2 days the mixture was partitioned between AcOEt-brine. The aqueous layer was extracted with AcOEt (2×). The combined organic solutions were dried (MgSO$_4$), filtered and concentrated. The residue was purified by preparative TLC (PTLC) with CH$_2$Cl$_2$ as eluent to afford the azaindoline 6 (21 mg, 8%) as a solid. $^1$H NMR (400 MHz; CDCl$_3$) δ 3.04 (t, J=8.6 Hz, 2H), 4.08 (t, J=8.6 Hz, 2H), 7.45-7.51 (m, 3H), 7.56-7.60 (m, 1H), 8.08 (m, 2H), 8.18 (m, 1H).

Use of 5-bromo-7-azaindoline 4 in the metal-halogen exchange and subsequent reactions Reaction with Alkyl Halides. Synthesis of 5-methyl Derivative 9

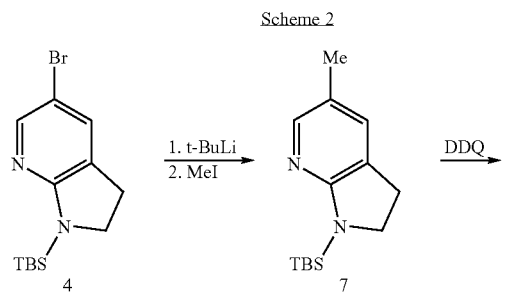

Scheme 2

1-(tert-Butyl-dimethyl-silanyl)-5-methyl-2,3-dihydro-1H-pyrrolo[2,3-b]pyridine (7)

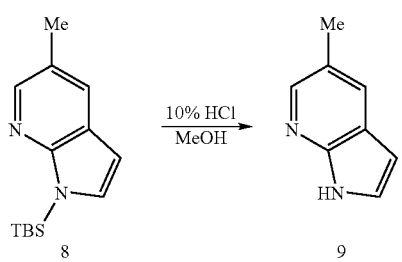

To a stirred and cooled (−78° C.) solution of bromide 4 (0.20 g, 0.64 mmol) in Et$_2$O (2.5 mL) was added dropwise a 1.5 M solution of tert-BuLi in pentane (0.89 mL, 1.34 mmol). After 38 min MeI (0.1 mL, 1.61 mmol) was added dropwise and the mixture allowed to gradually warm to r.t. After 12 h the mixture was partitioned between CHCl$_3$ and saturated aqueous NaHCO$_3$ solution. The aqueous layer was extracted with CHCl$_3$ (2×). The combined organic extracts were dried (MgSO$_4$), and concentrated to afford 7 as a yellow oily residue, which was used directly in the next step without purification.

1-(tert-Butyl-dimethyl-silanyl)-5-methyl-1H-pyrrolo[2,3-b]pyridine (8)

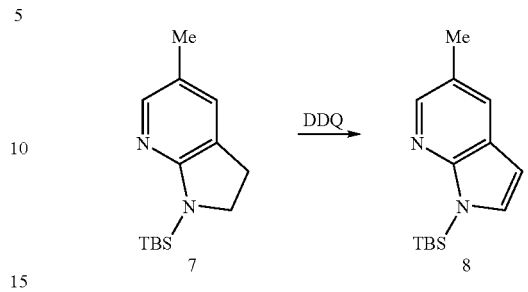

To a stirred solution of the crude azaindoline 7 (0.64 mmol) in CH$_2$Cl$_2$ (10 mL) was added DDQ (145 mg, 0.64 mmol) in one portion. After 20 min the resulting black mixture was diluted with saturated aqueous NaHCO$_3$ solution and stirred vigorously for 15 min. The aqueous layer was extracted with CHCl$_3$ (2×) and the combined organic solutions were dried (MgSO$_4$), filtered and concentrated to afford azaindole 8 as a brown oil, which was used directly in the next step without purification.

5-Methyl-1H-pyrrolo[2,3-b]pyridine (9)

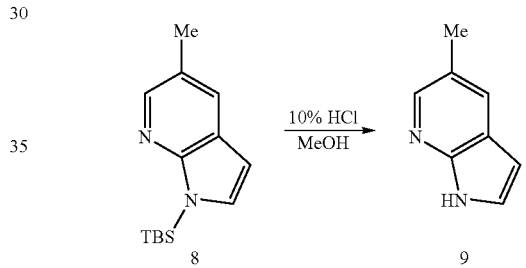

To a stirred solution of the crude azaindole 8 (0.64 mmol) in MeOH (6 mL) was added a 10% solution of HCl in methanol (3 mL). After 20 min the mixture was concentrated and partitioned between AcOEt and saturated aqueous NaHCO$_3$ solution. The aqueous layer was extracted with AcOEt (2×) and the combined organic solutions were dried (MgSO$_4$), filtered and concentrated. The residue was purified by PTLC using 5% MeOH in CH$_2$Cl$_2$ to afford the desired methyl derivative 9 (68 mg, 81% over 3 steps). $^1$H NMR (400 MHz; CDCl$_3$) δ 2.45 (s, 3H), 6.42 (d, J=3.4 Hz, 1H), 7.34 (d, J=3.4 Hz, 1H), 7.76 (d, J=1.7 Hz, 1H), 8.19 (d, J=1.7 Hz, 1H), 10.92 (br s, NH).

Reaction with CO$_2$. Synthesis of Acid 12.

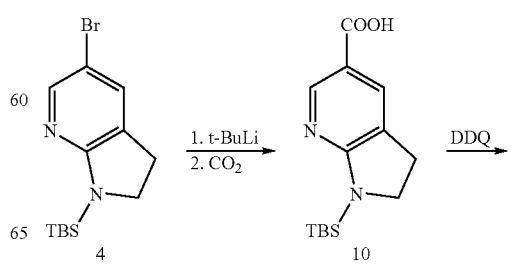

-continued

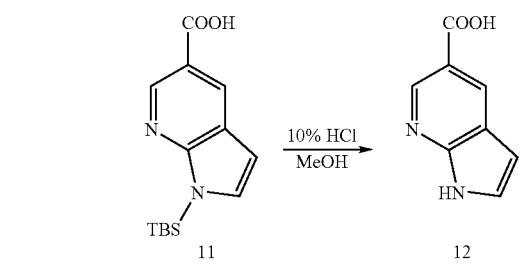

1-(tert-Butyl-dimethyl-silanyl)-2,3-dihydro-1H-pyrrolo[2,3-b]pyridine-5-carboxylic acid (10)

To a stirred and cooled (−78° C.) solution of the bromide 4 (205 mg, 0.65 mmol) in Et$_2$O (4 mL) was added dropwise a 1.5 M solution of tert-butyllithium in pentane (0.92 mL, 1.37 mmol). After 40 min., dry gaseous CO$_2$ was introduced into the reaction vessel. Progress of the reaction was followed by TLC analysis. After complete consumption of starting material 4 the reaction was quenched by the addition of saturated aqueous NaHCO$_3$ solution. The mixture was allowed to warm to room temperature, and diluted with CH$_2$Cl$_2$. The aqueous layer was extracted with CH$_2$Cl$_2$ (2×), and the combined organic solutions were dried (MgSO$_4$), filtered and concentrated. The residual yellow oil was dissolved in CH$_2$Cl$_2$:MeOH=20:1 and filtered through silicagel pad. The filtrate was concentrated and used directly in the next step.

1H-Pyrrolo[2,3-b]pyridine-5-carboxylic acid (12)

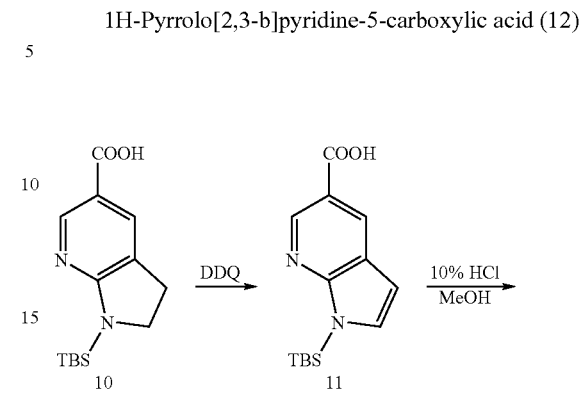

A solution of crude acid 10 in CH$_2$Cl$_2$ (5 mL) was treated with DDQ in small portions until TLC analysis revealed no starting material left. The mixture was concentrated to afford a solid residue containing azaindole 11. The residue was dissolved in a 5% solution of HCl in MeOH (5 mL), and stirred at r.t. After 1.5 h the mixture was concentrated and diluted with CHCl$_3$ and saturated brine. The mixture was basified with 50% NaOH solution to pH 11. The organic layer was discarded. The aqueous layer was neutralized with 6 M HCl and extracted with AcOEt (4×). The combined organic extracts were dried (MgSO$_4$), filtered and concentrated. The residue was purified by PTLC using CH$_2$Cl$_2$:MeOH=9:1 as eluent to afford acid 12 (3.19 mg, 3% over 3 steps). $^1$H NMR (400 MHz; CD$_3$OD) δ 6.58 (d, J=3.5 Hz, 1H), 7.42 (d, J=3.5 Hz, 1H), 8.58 (d, J=2.0 Hz, 1H), 8.85 (d, J=1.7 Hz, 1H).

Reaction with DMF. Synthesis of Alcohol 15 and Aldehyde 16.

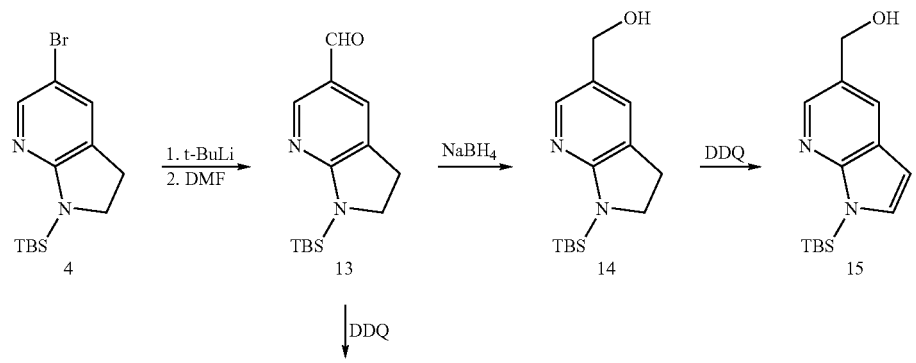

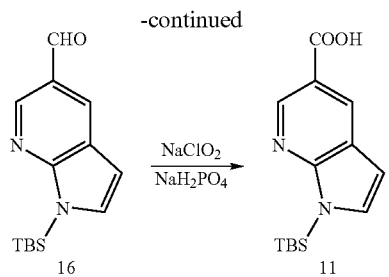

1-(tert-Butyl-dimethyl-silanyl)-2,3-dihydro-1H-pyrrolo[2,3-b]pyridine-5-carbaldehyde (13)

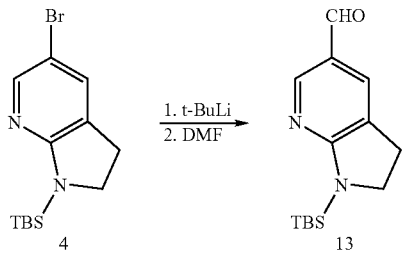

To a stirred and cooled (−78° C.) solution of the bromide 4 (5.00 g, 15.96 mmol) in Et$_2$O (92 mL) was added dropwise 1.5 M solution of tert-butyllithium in pentane (22.3 mL, 33.5 mmol). After 45 min additional stirring at −78° C., DMF (5.6 mL, 72.3 mmol) was added dropwise, and the mixture was allowed to slowly warm to r.t. After 20 h the mixture was partitioned between saturated aqueous NaHCO$_3$ solution and CH$_2$Cl$_2$. The organic layer was separated, dried (MgSO$_4$), and concentrated to afford the crude aldehyde 13 (4.32 g). $^1$H NMR (400 MHz; CDCl$_3$) δ 0.32 (s, 6H), 0.92 (s, 9H), 3.02 (m, 2H), 3.70 (m, 2H), 7.55 (d, J=2.0 Hz, 1H), 8.16 (d, J=2.0 Hz, 1H), 9.61 (s, 1H).

[1-(tert-Butyl-dimethyl-silanyl)-2,3-dihydro-1H-pyrrolo[2,3-b]pyridin-5-yl]-methanol (14)

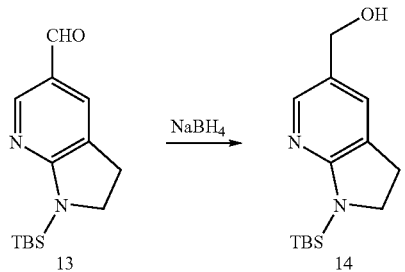

To a stirred and cooled (0° C.) solution of crude 13 (2.77 g, 10.6 mmol) in EtOH (100 mL) was added NaBH$_4$ (0.48 mg, 12.7 mmol) in a single portion. The mixture was allowed to warm to r.t. After 20 h the mixture was concentrated and partitioned between CH$_2$Cl$_2$-brine. The organic layer was dried (MgSO$_4$) and concentrated. The residue was purified by SGC with CH$_2$Cl$_2$:MeOH as eluent (gradient up to 5% MeOH) to afford alcohol 14 (0.67 g, 24%). $^1$H NMR (400 MHz; CDCl$_3$) δ 0.31 (s, 6H), 0.94 (s, 9H), 2.97 (t, J=8.2 Hz, 2H), 3.65 (t, J=8.2 Hz, 2H), 4.39 (s, 2H), 7.19 (s, 1H), 7.69 (s, 1H).

[1-(tert-Butyl-dimethyl-silanyl)-1H-pyrrolo[2,3-b]pyridin-5-yl]-methanol (15)

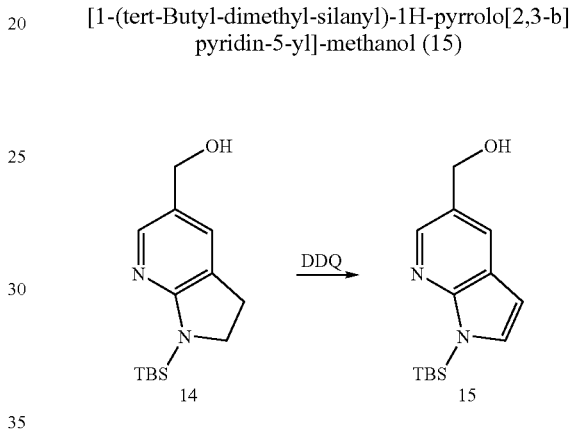

DDQ (53 mg, 0.23 mmol) was added in three equal portions to a stirred solution of alcohol 14 (54 mg, 0.20 mmol) in a mixture of CH$_2$Cl$_2$ (15 mL) and 0.2 M pH 7 phosphate buffer (0.15 mL). When TLC analysis showed complete consumption of the starting material, the mixture was diluted with saturated aqueous NaHCO$_3$ (16 mL) and stirred vigorously for 1 h. Then the mixture was extracted with AcOEt (2×). The combined organic extracts were washed with saturated brine (1×), dried (MgSO$_4$) and concentrated. The residue was purified by PTLC with benzene as eluent to afford alcohol 15 (16 mg, 31%). $^1$H NMR (400 MHz; CDCl$_3$) δ 0.63 (s, 6H), 0.93 (s, 9H), 4.77 (s, 2H), 6.52 (d, J=3.5 Hz, 1H), 7.26 (d, J=3.5 Hz, 1H), 7.89 (d, J=2.0 Hz, 1H), 8.28 (d, J=2.0 Hz, 1H).

1-(tert-Butyl-dimethyl-silanyl)-1H-pyrrolo[2,3-b]pyridine-5-carbaldehyde (16)

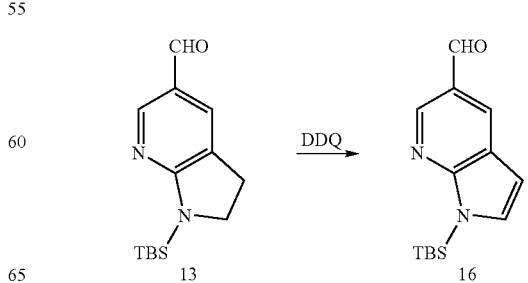

To a stirred solution of the alcohol 13 (54 mg, 0.20 mmol) in a mixture of CH$_2$Cl$_2$ (15 mL) and 0.2 M pH 7 phosphate buffer (0.15 mL) was added DDQ (53 mg, 0.23 mmol) in three equal portions. When TLC analysis showed complete consumption of the starting material, the mixture was diluted with saturated aqueous NaHCO$_3$ (16 mL) and stirred vigorously for 1 h. The mixture was then extracted with AcOEt (2×). The combined organic solutions were washed with saturated brine (1×), dried (MgSO$_4$) and concentrated. The residue was purified by PTLC with benzene as eluent to afford aldehyde 16 (11 mg, 21%). $^1$H NMR (400 MHz; CDCl$_3$) δ 0.66 (s, 6H), 0.94 (s, 9H), 6.67 (d, J=3.5 Hz, 1H), 7.34 (d, J=3.5 Hz, 1H), 8.37 (d, J=2.0 Hz, 1H), 8.76 (d, J=2.0 Hz, 1H), 10.11 (s, 1H).

1-(tert-Butyl-dimethyl-silanyl)-1H-pyrrolo[2,3-b]pyridine-5-carboxylic acid (11)

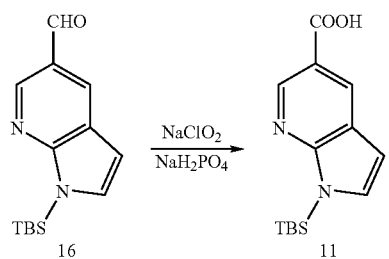

To a stirred and cooled (0° C.) solution of aldehyde 16 (115 mg, 0.44 mmol) in tert-butanol (3.1 mL) and 2-methyl-2-butene (0.77 mL) was added a solution of NaClO$_2$ (194 mg, 2.1 mmol) and NaH$_2$PO$_4$.H$_2$O (244 mg, 1.8 mmol) in water (2.31 mL) dropwise. When 16 was consumed (TLC) the mixture was partitioned between AcOEt and water. The organic layer was washed with saturated brine (1×), dried (MgSO$_4$), filtered and concentrated to afford acid 11 (20 mg, 16%) as an off-white solid. $^1$H NMR (400 MHz; CDCl$_3$) δ 0.66 (s, 6H), 0.94 (s, 9H), 6.65 (s, 1H), 7.32 (s, 1H), 8.61 (s, 1H) and 9.03 (s, 1H).

Metal-Metal Exchange—Stannylation. Synthesis of Benzyl Derivative 18.

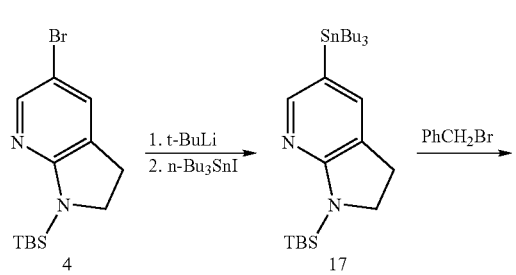

-continued

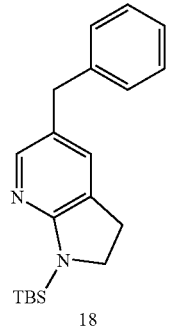

1-(tert-Butyl-dimethyl-silanyl)-5-tributylstannanyl-2,3-dihydro-1H-pyrrolo[2,3-b]pyridine (17)

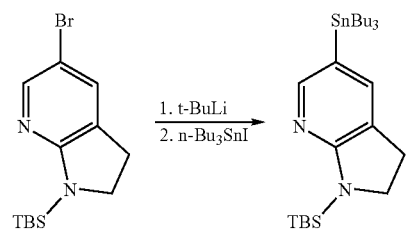

To a stirred and cooled (−90° C.) solution of bromide 4 (206 mg, 0.66 mmol) in THF (2.5 mL) was added dropwise 1.5 M solution of tert-butyllithium in pentane (1 mL, 1.51 mmol). After 35 min additional stirring at −90° C., tri-n-butyltin iodide (0.23 mL, 0.79 mmol) was added in one portion. The mixture was stirred at −90° C. for 10 min, −78° C. for 40 min, and then allowed to warm to r.t. The mixture was partitioned between AcOEt-brine. The aqueous layer was extracted with AcOEt (3×) and the combined organic solutions were dried (MgSO$_4$), and concentrated to afford the crude stannane 17, which was used in the next step without purification.

5-Benzyl-2,3-dihydro-1H-pyrrolo[2,3-b]pyridine (18)

To a stirred solution of the crude stannane 17 (172 mg, 0.33 mmol) in THF (2.5 mL) was added PhCH$_2$Br (0.03 mL, 0.27 mmol) and (Ph$_3$P)$_2$PdCl$_2$ (5 mg, 0.007 mmol). The mixture was refluxed under N₂ for 19 h, cooled, and partitioned between AcOEt-brine. The aqueous layer was extracted with AcOEt (2×). The combined organic solutions were dried (MgSO₄), and concentrated in vacuum. The residual yellow oil was dissolved in MeOH (3 mL) and treated with a 10% solution of HCl in MeOH (2 mL). The mixture was stirred for 2.5 h, neutralized with saturated aqueous NaHCO₃ solution and extracted with AcOEt (2×). The combined organic extracts were dried (MgSO₄), concentrated, and purified by PTLC with CH₂Cl₂:MeOH=95:5 as eluent to afford the 5-benzyl derivative 18 (8 mg, 11% over 2 steps). ¹H NMR (400 MHz; CDCl₃) δ 2.99 (t, J=8.1 Hz, 2H), 3.60 (t, J=8.3 Hz, 2H), 3.79 (s, 2H), 7.06-7.31 (m, 7H), 7.69 (br s, NH).

Reaction with Aldehyde. Synthesis of Alcohol 19 and Ketone 20.

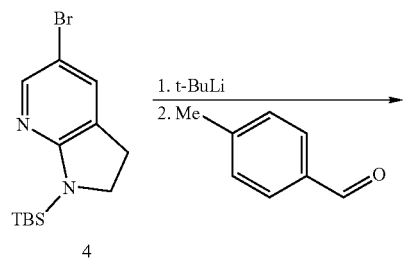

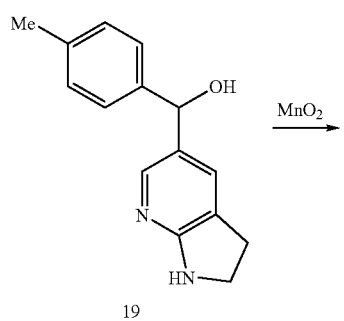

(2,3-Dihydro-1H-pyrrolo[2,3-b]pyridin-5-yl)-p-tolyl-methanol (19)

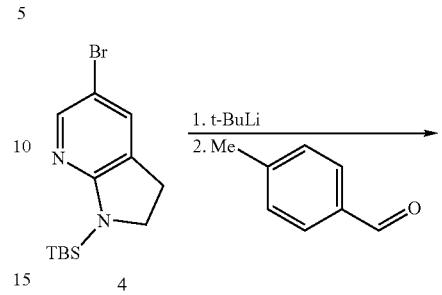

To a stirred and cooled (−78° C.) solution of the bromide 4 (100 mg, 0.32 mmol) in Et₂O (1.8 mL) was added dropwise 1.5 M solution of tert-butyllithium in pentane (0.45 mL, 0.67 mmol). The mixture was stirred for an additional 0.6 h at −78° C., p-tolylaldehyde (0.04 mL, 0.32 mmol) was added, and the mixture slowly allowed to warm to r.t. After 18 h the mixture was partitioned between AcOEt-brine. The aqueous layer was extracted with AcOEt (2×). The combined organic solutions were dried (MgSO₄), concentrated, and the residue was purified by PTLC with CH₂Cl₂:MeOH=95:5 as eluent to afford alcohol 19 (15 mg, 19%) as a white solid. ¹H NMR (400 MHz; CDCl₃) δ 2.34 (s, 3H), 5.99 (s, 1H), 6.45 (d, J=3.5 Hz, 1H), 7.16 (d, J=7.8 Hz, 2H), 7.30-7.32 (m, 3H), 7.93 (d, J=1.8 Hz, 1H), 8.32 (d, J=2.0 Hz, 1H) and 9.77 (br s, NH).

(1H-Pyrrolo[2,3-b]pyridin-5-yl)-p-tolyl-methanone (20)

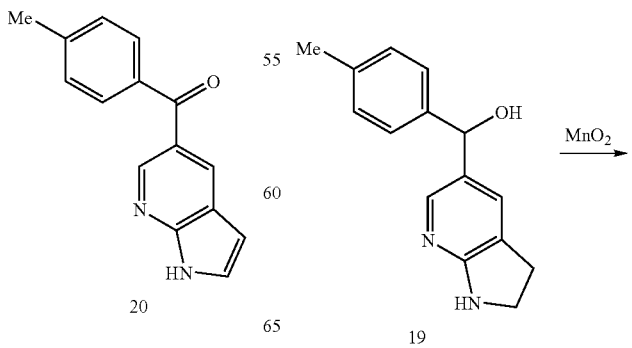

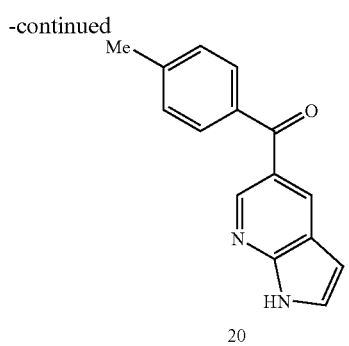

To a stirred solution of the alcohol 20 (15 mg, 0.06 mmol) in CHCl₃ (1.2 mL) was added activated MnO₂ (5.4 mg, 0.06 mmol) in one portion. After 0.5 h the mixture was filtered through a pad of silica and the filtrate evaporated. The residue was purified by PTLC with CH₂Cl₂:MeOH=95:5 as eluent to afford ketone 20 (12.5 mg, 88%) as a white solid. ¹H NMR (400 MHz; CDCl₃) δ 2.47 (s, 3H), 6.63 (d, J=3.3 Hz, 1H), 7.32 (d, J=8.1 Hz, 2H), 7.44 (d, J=3.0 Hz, 1H), 7.75 (d, J=8.1 Hz, 2H), 8.43 (d, J=1.8 Hz, 1H), 8.83 (d, J=1.8 Hz, 1H) and 10.14 (br s, NH).

Reaction with Halosilanes. Synthesis of TMS Derivative 22.

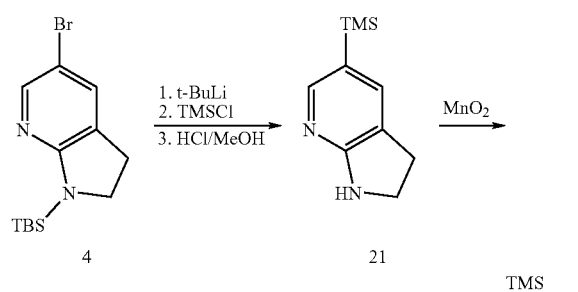

5-Trimethylsilanyl-2,3-dihydro-1H-pyrrolo[2,3-b]pyridine (21)

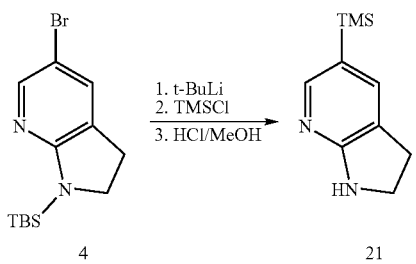

To a stirred and cooled (−78° C.) solution of bromide 4 (600 mg, 1.91 mmol) in Et₂O (10.8 mL) was added 1.5 M t-BuLi in pentane (2.68 mL, 4.02 mmol) dropwise, followed after 40 min by dropwise addition of TMSCl (0.36 mL, 3.83 mmol). The mixture was allowed to warm slowly to r.t. After 18 h the mixture was quenched by the addition of water and then extracted with AcOEt. The organic extract was washed with saturated brine, dried (MgSO₄), filtered and concentrated to afford the crude disilylated azaindoline (508 mg). This was diluted with MeOH (15.6 mL) and 10% HCl (7.8 mL) and stirred vigorously for 20 min. The mixture was basified with saturated NaHCO₃ solution and extracted with AcOEt (2×). The combined organic extracts were dried (MgSO₄), and concentrated to afford the desired 21 (367 mg, quantitative over 2 steps). ¹H NMR (400 MHz; CDCl₃) δ 0.22 (s, 9H), 3.04 (m, 2H), 3.60 (t, J=8.3 Hz, 2H), 4.58 (br s, NH), 7.34 (m, 1H), 7.88 (m, 1H).

5-Trimethylsilanyl-1H-pyrrolo[2,3-b]pyridine (22)

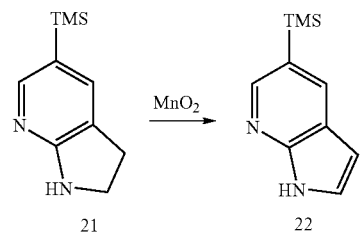

To a stirred solution of the azaindoline 21 (20 mg, 0.10 mmol) in CH₂Cl₂ (2 mL) was added oven activated MnO₂ (9 mg, 0.10 mmol) in one portion. After 18 h the mixture was filtered through a silica pad. The pad was washed with AcOEt and the combined organic solutions evaporated to afford the azaindole 22 (17 mg, 86%). ¹H NMR (400 MHz; CDCl₃) δ 0.35 (s, 9H), 6.50 (d, J=3.5 Hz, 1H), 7.35 (d, J=3.5 Hz, 1H), 8.10 (d, J=1.5 Hz, 1H), 8.40 (d, J=1.5 Hz, 1H), 10.62 (br s, NH).

Participation of 5-bromoindolines in Suzuki type reactions. Synthesis of 4-(dimethylamino)phenyl derivatives 23 and 24.

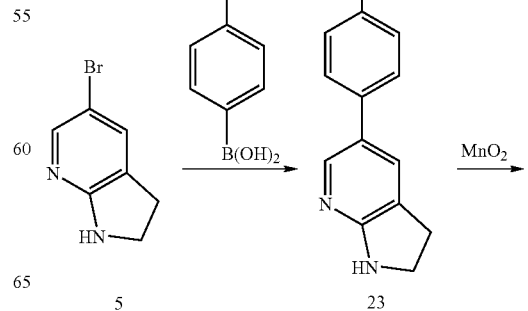

Dimethyl-[4-(1H-pyrrolo[2,3-b]pyridin-5-yl)-phenyl]-amine (24) and methyl-[4-(1H-pyrrolo[2,3-b]pyridin-5-yl)-phenyl]-amine (25)

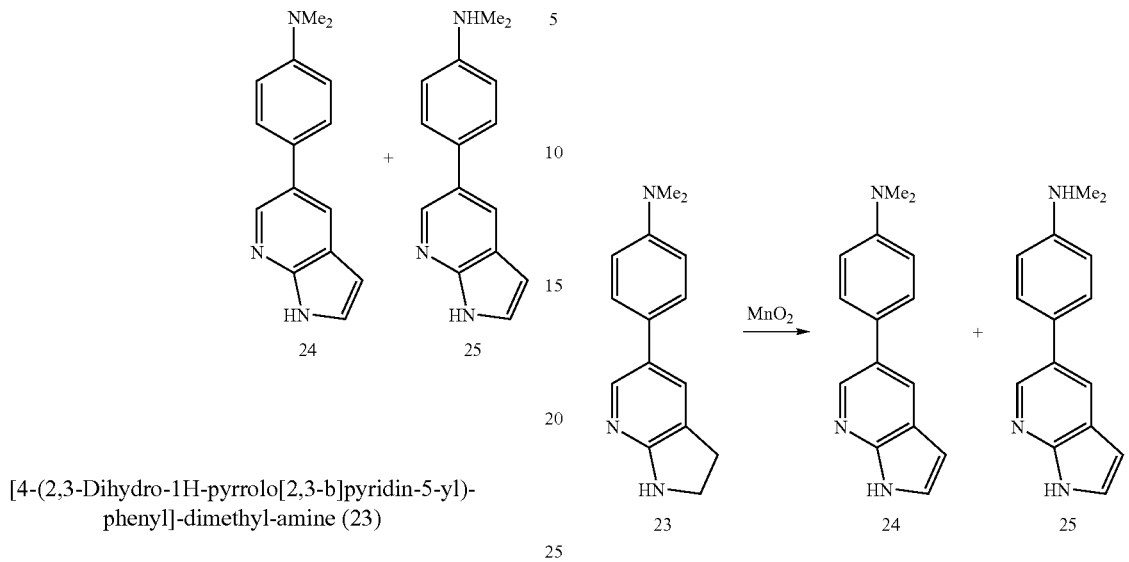

[4-(2,3-Dihydro-1H-pyrrolo[2,3-b]pyridin-5-yl)-phenyl]-dimethyl-amine (23)

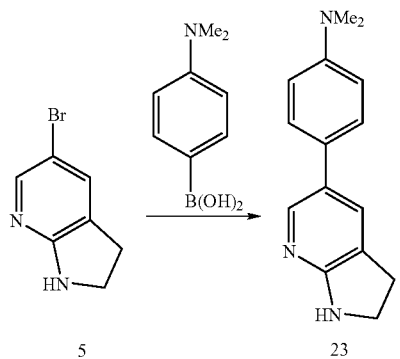

A mixture of 5 (29.0 g, 0.146 mol), 4-(dimethylamino)phenylboronic acid (36.05 g, 0.218 mol), LiCl (18.5 g, 0.441 mol), (PPh$_3$)$_2$PdCl$_2$ (8.60 g, 12.3 mmol) and 10% aqueous Na$_2$CO$_3$ (364 mL) in EtOH (870 mL):toluene (870 mL) was refluxed for 1 h 30 min. The reaction mixture was cooled to r.t., and poured into AcOEt:brine. The organic layer was separated and the aqueous layer was extracted with CH$_2$Cl$_2$ (10×500 mL). Combined organic solutions were dried (MgSO$_4$), concentrated and redissolved in CH$_2$Cl$_2$ (1.5 L). The solution was mixed with silicagel (250 mL; Kieselgel 60, 230-400 mesh). Solvent was evaporated and the residual solid loaded on a silicagel column for separation. Purification by means of SGC with CH$_2$Cl$_2$:MeOH as eluent afforded 17.25 g (49%) of desired 23 as tan powder. $^1$H NMR (400 MHz, CDCl$_3$) δ 2.98 (s, 6H), 3.11 (tt, J=8.3, 1.0 Hz, 2H), 3.65 (t, J=8.3 Hz, 2H), 4.44 (bs, 1H), 6.79 (d, J=8.8 Hz, 2H), 7.38 (d, J=8.8 Hz, 2H), 7.46 (dt, J=2.0, 1.2 Hz, 1H), 8.02 (dt, J=2.0, 0.9 Hz, 1H).

To a solution of 23 (11.5 g, 48.5 mmol) in CH$_2$Cl$_2$ (1 L) was added portionwise over 2 h solid MnO$_2$ (~75 g, activated by heating at 130° C.) until the TLC showed no starting material remaining. The reaction mixture was filtered and the filtrate concentrated. The residual dark brown solid was purified by SGC using AcOEt:hexane (1:1, dry loading) as eluent to afford 24 (9.50 g, 83%) as a light orange solid; $^1$H NMR (400 MHz, CDCl3) δ 3.04 (s, 6H), 6.56 (dd, J=3.4, 1.6 Hz, 1H), 6.89 (d, J=8.8 Hz, 2H), 7.41 (dd, J=3.4, 2.3 Hz, 1H), 7.57 (d, J=8.8 Hz, 2H), 8.12 (d, J=2.1 Hz, 1H), 8.58 (d, J=2.1 Hz, 1H), 10.40-10.60 (bs, NH). The $^1$H NMR also showed a small amount of 25 (about 8% mol), which could not be separated from 24.

Participation of 5-bromoindoles in Suzuki type reactions. Synthesis of 5-substituted 7-azaindoles 24, 28, and 29.

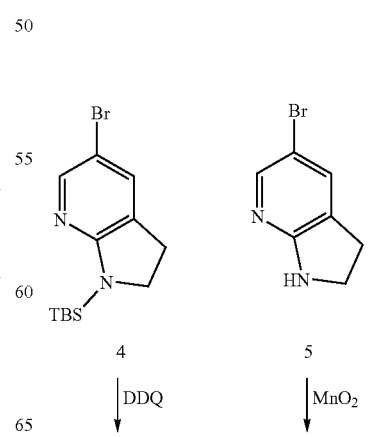

-continued

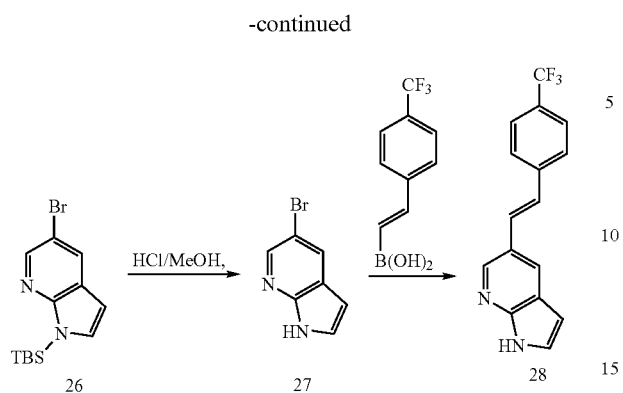

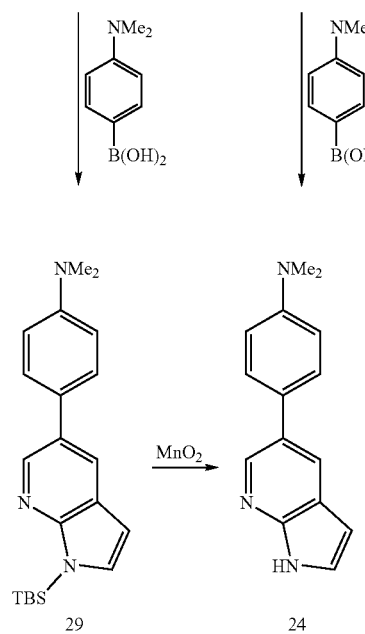

5-Bromo-1-(tert-butyl-dimethyl-silanyl)-1H-pyrrolo[2,3-b]pyridine (26)

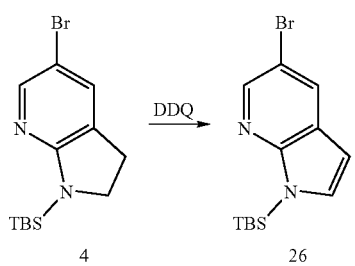

DDQ (about 380 mg, 1.68 mmol) was added in portions to a solution of 4 (525 mg, 1.68 mmol) in a mixture of CH$_2$Cl$_2$ (90 mL) and 0.2 M phosphate buffer pH 7 solution (910 µL) until full consumption of the starting material (TLC). Then, saturated aqueous NaHCO$_3$ solution (22 mL) was added, and the reaction mixture stirred for 0.5 h. The organic layer was separated and the aqueous layer was extracted with CH$_2$Cl$_2$ (3×20 mL). The combined organic solutions were dried (MgSO$_4$), concentrated and purified by SGC with hexane: CH$_2$Cl$_2$ as eluent (in gradient up to 20% CH$_2$Cl$_2$) to give 26 (505 mg, 97%) as a clear oil; $^1$H NMR (400 MHz, CDCl$_3$) δ 0.62 (s, 6H), 0.93 (s, 9H), 6.47 (d, J=3.5 Hz, 1H), 7.24 (d, J=3.5 Hz, 1H), 7.97 (d, J=2.2 Hz, 1H), 8.28 (d, J=2.2 Hz, 1H).

5-Bromo-1H-pyrrolo[2,3-b]pyridine (27)

Method 1—from 26

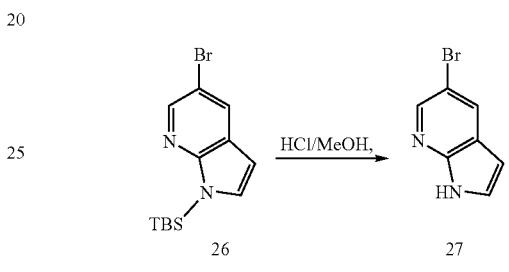

To a stirred solution of the TBS derivative 26 (1.01 g, 3.3 mmol) in MeOH (10 mL) was added a 10% solution of HCl in MeOH (7 mL). After 8 min the solvents were evaporated and the residue was partitioned between AcOEt and saturated aqueous NaHCO$_3$. The aqueous layer was extracted with AcOEt (3×). The combined organic solutions were dried (MgSO$_4$), concentrated and purified by PTLC with CH$_2$Cl$_2$: MeOH=95:5 as eluent to afford the bromo derivative 27 (0.60 g, 94%). $^1$H NMR (400 MHz; CDCl$_3$) δ 6.47 (dd, J=2.0, 3.5 Hz, 1H), 7.37 (dd, J=2.5, 3.5 Hz, 1H), 8.08 (d, J=2.0 Hz, 1H), 8.36 (d, J=2.0 Hz, 1H), 10.24 (br s, H).

Method 2—from 5

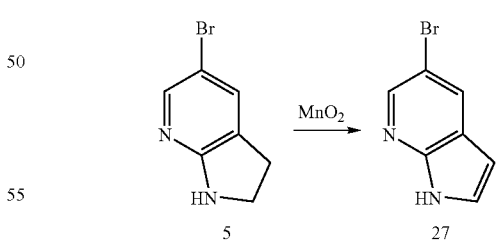

To a stirred solution of azaindoline 5 (7.00 g, 35.2 mmol) in CH$_2$Cl$_2$ (664 mL) was added activated MnO$_2$ (3.06 g, 35.2 mmol), and progress of the reaction was monitored by $^1$H NMR of reaction aliquots. After 3 days the mixture was filtered through a pad of silica, and the pad was washed with EtOAc. The filtrates were concentrated to afford the azaindole 27 (6.98 g, 100%) as a brown solid. $^1$H NMR data as in Method 1.

Dimethyl-[4-(1H-pyrrolo[2,3-b]pyridin-5-yl)-phenyl]-amine (24)

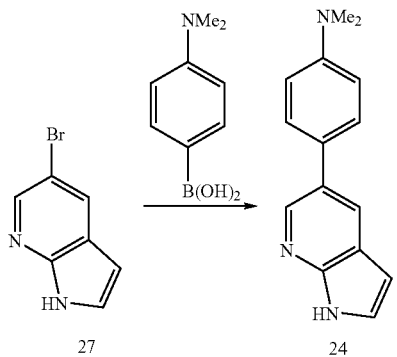

A mixture of bromide 27 (6.00 g, 30.4 mmol), lithium chloride (3.84 g, 90.8 mmol), 4-(N,N-dimethylaminophenyl)boronic acid (7.53 g, 45.7 mmol), toluene (171 mL), EtOH (171 mL), 1 M aqueous Na$_2$CO$_3$ solution (76.2 mL, 76.2 mmol) and (PPh$_3$)$_2$PdCl$_2$ (60 mg, 0.080 mmol) was refluxed (bath temp. 105° C.) in the dark under nitrogen for 22 h. The mixture was then concentrated to dryness and the residue partitioned between CH$_2$Cl$_2$-water. The layers were separated and the aqueous layer was extracted with CH$_2$Cl$_2$. The combined organic solutions were dried (MgSO$_4$), concentrated and purified by SGC using AcOEt as eluent to afford the product 24 (6.32 g, 88%) as a pale yellow solid. $^1$H NMR (400 MHz; CDCl$_3$) δ 2.98 (s, 6H), 3.11 (tt, J=8.3, 1.0 Hz, 2H), 3.65 (t, J=8.3 Hz, 2H), 4.44 (bs, 1H), 6.79 (d, J=8.8 Hz, 2H), 7.38 (d, J=8.8 Hz, 2H), 7.46 (dt, J=2.0, 1.2 Hz, 1H), 8.02 (dt, J=2.0, 0.9 Hz, 1H).

5-[2-(4-Trifluoromethyl-phenyl)-vinyl]1H-pyrrolo[2,3-b]pyridine (28)

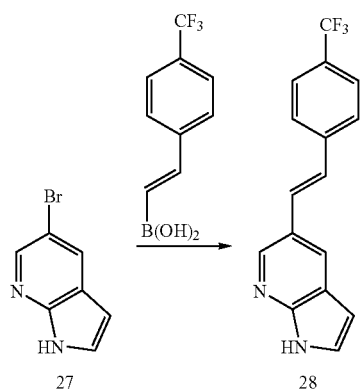

To a solution of bromide 27 (76 mg, 0.39 mmol), lithium chloride (49 mg, 1.16 mmol), trans-2[4-(trifluoromethyl)-phenyl]vinyl boronic acid (125 mg, 0.58 mmol) in a mixture of toluene (3 mL), EtOH (3 mL) and 1 M aqueous Na$_2$CO$_3$ solution (0.96 mL, 0.96 mmol) was added (PPh$_3$)$_2$PdCl$_2$ (27 mg, 0.04 mmol) in one portion. The mixture was heated in the dark to 105° C. under a nitrogen atmosphere for 20 h, filtered through a pad of cotton wool and concentrated. The residue was purified by PTLC with CH$_2$Cl$_2$:MeOH=98:2 as eluent to afford styrene 28 (51 mg, 46%) as a pale yellow solid. $^1$H NMR (400 MHz; CDCl$_3$) δ 6.55 (dd, J=2.0, 3.5 Hz, 1H), 7.15 (d, J=16.3 Hz, 1H), 7.31 (d, J=16.3 Hz, 1H), 7.35 (m, 1H), 7.62 (s, 4H), 8.13 (d, J=1.8 Hz, 1H), 8.50 (m, 1H), 9.17 (br s, NH).

{4-[1-(tert-Butyl-dimethyl-silanyl)-1H-pyrrolo[2,3-b]pyridin-5-yl]-phenyl}-dimethyl-amine (29)

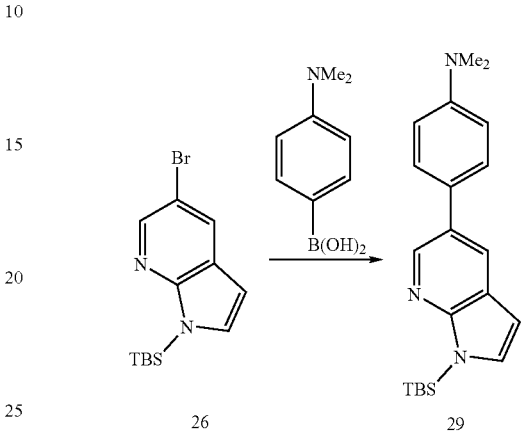

A mixture of bromide 26 (500 mg, 1.61 mmol), lithium chloride (204 mg, 4.82 mmol), 4-(N,N-dimethylaminophenyl)boronic acid (398 mg, 1.61 mmol), toluene (9.6 mL), EtOH (9.6 mL), 1 M aqueous Na$_2$CO$_3$ solution (4.0 mL, 4.0 mmol) and (PPh$_3$)$_2$PdCl$_2$ (95 mg, 0.135 mmol) was stirred in the dark under nitrogen at r.t. overnight and at 105° C. for 1 h. The mixture was then partitioned between AcOEt (20 mL) and brine (20 mL). The layers were separated and the aqueous layer was extracted with AcOEt (3×20 mL). The combined organic solutions were dried (MgSO$_4$), concentrated and purified by SGC using hexane:CH$_2$Cl$_2$ as eluent (up to 30% CH$_2$Cl$_2$) to give 29 as a white solid (423 mg, 75%); $^1$H NMR (400 MHz, CDCl3) δ 0.56 (s, 6H), 0.87 (s, 9H), 2.89 (s, 6H), 6.45 (d, J=3.5 Hz, 1H), 6.74 (d, J=8.8 Hz, 2H), 7.15 (d, J=3.4 Hz, 1H), 7.44 (d, J=8.8 Hz, 2H), 7.90 (d, J=2.3 Hz, 1H), 8.42 (d, J=2.2 Hz, 1H).

Participation of 5-bromoindoles in the Stille Reaction. Synthesis of Thiophene Derivative 30.

5-Thiophen-2-yl-1H-pyrrolo[2,3-b]pyridine (30)

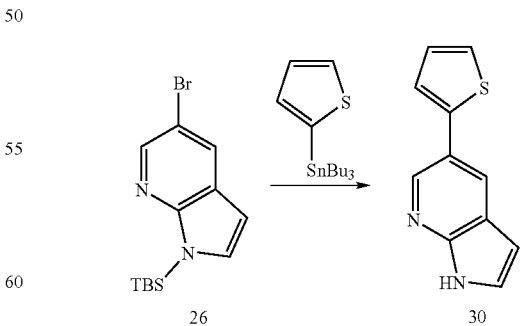

A solution of bromide 26 (150 mg, 0.48 mmol), 2-(tributylstannyl)thiophene (270 mg, 0.72 mmol), tri-o-tolylphosphine (29 mg, 0.10 mmol) and PdCl$_2$(MeCN)$_2$ (12.5 mg, 0.05 mmol) in toluene (3 mL) was stirred at 85° C. for 18 h under N₂. The mixture was partially purified by PTLC using hexane:AcOEt=200:1 to afford a mixture of the desired product 30 and tin-containing impurities (205 mg). This mixture was dissolved in CHCl₃ and extracted with 10% aqueous HCl (4×). The combined aqueous solutions were washed with CHCl₃ (3×) and basified to pH 12 with 50% NaOH. The aqueous layer was extracted with CHCl₃ (3×) and the combined organic extracts dried (MgSO₄), filtered and evaporated to afford the azaindole 30 (22.7 mg, 23%) as a white solid. ¹H NMR (400 MHz; CDCl₃) 6.55 (dd, J=3.5, 1.8 Hz, 1H), 7.13 (dd, J=5.2, 3.5 Hz, 1H), 7.30-7.33 (m, 2H), 7.41 (dd, J=3.5, 2.4 Hz, 1H), 8.16 (d, J=2.0 Hz, 1H), 8.64 (br s, 1H), 10.45 (br s, NH).

Palladium-catalysed installation of boronic acid/ester functionality at C(5) of the 7-azaindole system. Synthesis of 5-(hetero)aryl derivatives 33, 35 and 37 via Suzuki reaction.

5-(4,4,5,5-Tetramethyl-[1,3,2]dioxaborolan-2-yl)-1H-pyrrolo[2,3-b]pyridine (31)

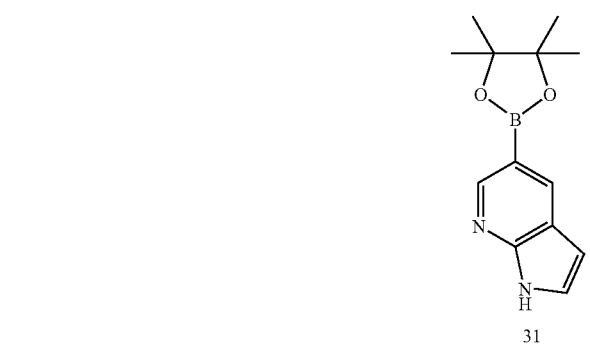

A mixture of 27 (500 mg, 2.54 mmol), [1,1'-bis(diphenylphosphino)ferrocene]dichloropalladium. HCl complex [PdCl₂(dppf)] (24.0 mg, 0.0298 mmol), bis(pinacolato)diboron (966 mg, 3.81 mmol) and potassium acetate (747 mg, 7.61 mmol) in DMF (15 mL) were heated at 80° C. overnight. More palladium catalyst (24 mg) was added and the stirring continued overnight. The reaction mixture was cooled, poured onto water, extracted with ethyl acetate. The combined organic extracts were dried (MgSO₄) and concentrated. The residual solid was extracted with diethyl ether. The solution was concentrated to give 31 as a tan solid (650 mg, 112%).

5-(2-Phenoxy-pyridin-3-yl)-1H-pyrrolo[2,3-b]pyridine (33)

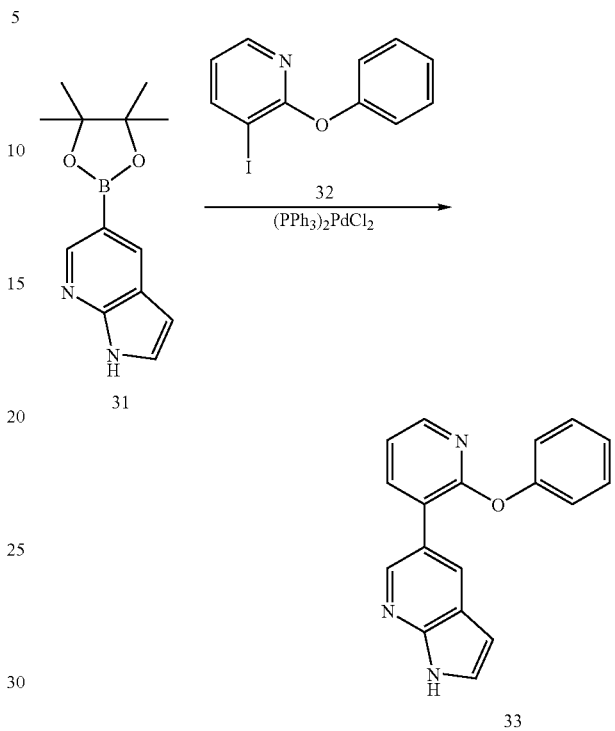

A mixture of pinacol ester 31 (200 mg, 0.88 mmol), iodide 32 (390 mg, 1.32 mmol), LiCl (112 mg, 2.63 mmol), PdCl₂(PPh₃)₂ (62 mg, 0.088 mmol), 1.0 M aq. Na₂CO₃ (2.2 mL, 2.19 mmol) in EtOH (4.0 mL) and toluene (4.0 mL) were refluxed for 5 h. After cooling the reaction mixture was partitioned between EtOAc/brine. The aqueous layer was extracted with more EtOAc (2×) and the combined organic extracts were dried (MgSO₄) and concentrated. The residue was purified by silicagel chromatography using EtOAc:hexane (1:1) (gradient elution) to give 33 (106 mg, 42%); ¹H NMR (400 MHz, CDCl₃) δ 6.26 (bs, 4H), 6.55 (s, 1H), 7.38 (bs, 3H), 7.82 (s, 1H), 8.18 (s, 1H), 8.27 (s, 1H), 8.62 (s, 1H), 10.73 (bs, NH).

Pyrimidin-2-yl-[2-(1H-pyrrolo[2,3-b]pyridin-5-yl)-phenyl]-amine (35)

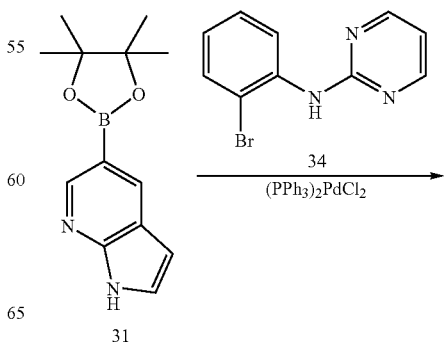

-continued

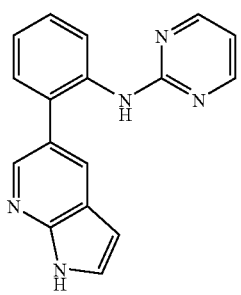

35

According to the above protocol, 31 (100 mg, 0.438 mmol), 34 (164 mg, 0.658 mmol), LiCl (56 mg, 1.32 mmol), PdCl$_2$(PPh$_3$)$_2$ (31 mg, 0.0438 mmol), and 1.0 M aq. Na$_2$CO$_3$ (1.10 mL, 1.10 mmol) in EtOH (2.6 mL) and toluene (2.6 mL) were refluxed for 24 h. Product 35 was isolated by silicagel chromatography using EtOAc:hexane (3:2) (gradient elution) as a light orange foam (45.7 mg, 36%); $^1$H NMR (400 MHz, CDCl$_3$) δ 6.33 (dd, J=3.5, 2.0 Hz, 1H), 6.69 (t, J=4.8 Hz, 1H), 7.17 (dt, J=8.7 Hz, 1.2 Hz, 1H), 7.23 (dd, J=5.8 Hz, 2.4 Hz, 1H), 7.29 (dd, J=7.6, 1.6 Hz, 1H), 7.42 (dt, J=8.4, 1.6 Hz, 1H), 7.89 (d, J=2.0 Hz, 1H), 8.05 (bs, NH), 8.16 (d, J=2.0 Hz, 1H), 8.28 (dd, J=8.2 Hz, 1.0 Hz, 1H), 8.40 (d, J=4.8 Hz, 2H), 11.02 (bs, NH).

[2-(1H-Pyrrolo[2,3-b]pyridin-5-yl)-phenyl]-carbamic acid tert-butyl ester (37)

Reaction was performed following the above protocol and using 31 (200 mg, 0.88 mmol), 36 (477 mg, 1.75 mmol), LiCl (112 mg, 2.63 mmol), PdCl$_2$(PPh$_3$)$_2$ (62 mg, 0.088 mmol), 1.0 M aq. Na$_2$CO$_3$ (2.19 mL, 2.19 mmol) in EtOH (5.2 mL) and toluene (5.2 mL) with refluxing overnight. Silicagel chromatography using EtOAc:hexane (1:4) (gradient elution) afforded 37 as an orange oil (187 mg, 69%); $^1$H NMR (400 MHz, CDCl$_3$) δ 1.25 (s, 9H), 6.48 (bs, NH), 6.57 (dd, J=3.5, 1.9 Hz, 1H), 7.12 (dt, J=7.5, 1.1 Hz, 1H), 7.23 (d, J=7.4 Hz, 1H), 7.39 (dt, J=8.6, 1.7 Hz, 1H), 7.42 (t, J=3.3 Hz, 1H), 7.93 (d, J=1.9 Hz, 1H), 8.12 (d, J=8.3 Hz, 1H), 8.30 (d, J=1.4 Hz, 1H), 10.09 (bs, NH).

Installation of boronic acid/ester functionality at C(5) of the 7-azaindole system via 5-lithio derivative. Synthesis of 5-(hetero)aryl derivative 41 using Suzuki reaction.

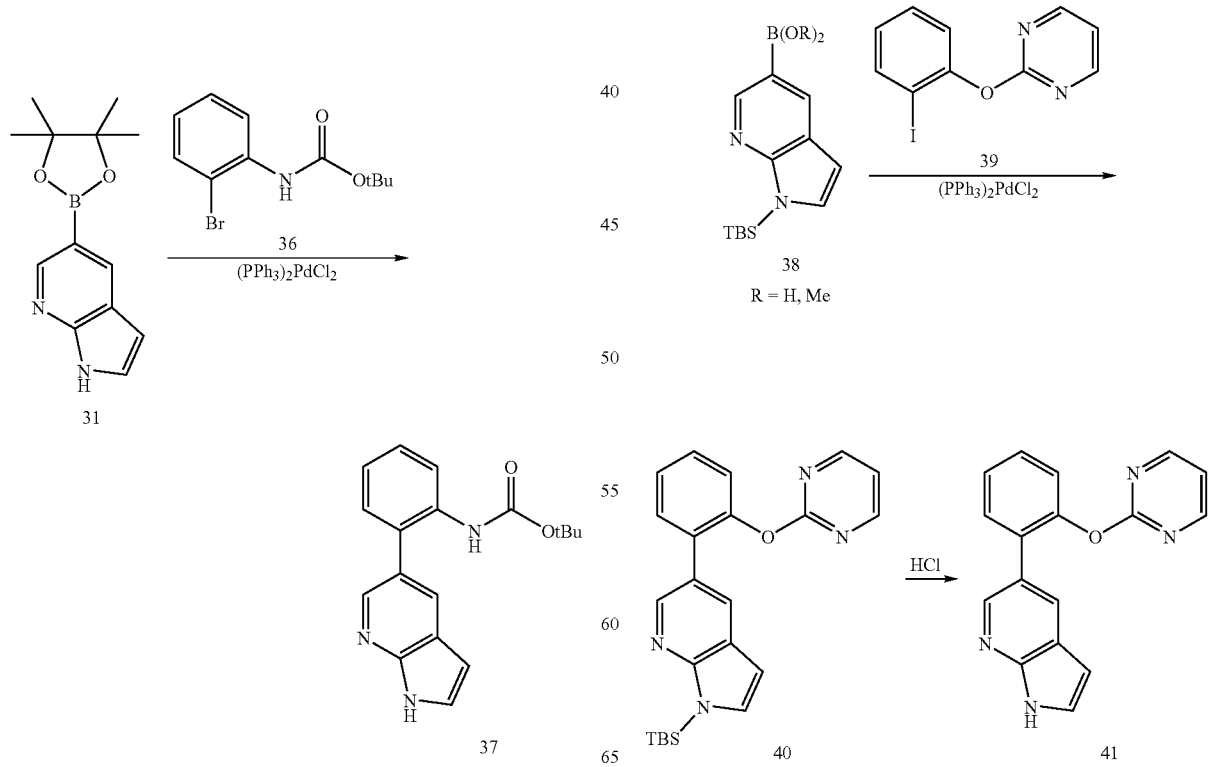

Synthesis of Boronic Derivative 38

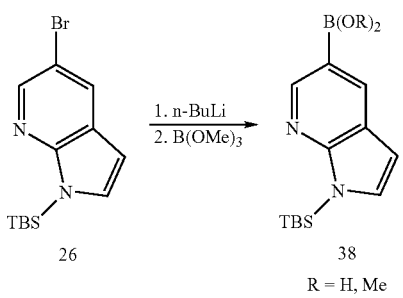

To n-BuLi (0.54 mL, 1.35 mmol, 2.5M in hexane) in THF (4.0 mL), cooled to −78° C., was added dropwise a solution of 26 (200 mg, 0.624 mmol) in THF (1.0 mL) and the solution stirred at −78° C. for 10 min. Trimethyl borate (87 μL, 0.77 mmol) was added in one portion and the reaction mixture stirred at −78° C. for 1 h then at room temperature for 2 h. The reaction mixture was poured onto a mixture of saturated aq. NaHCO$_3$/ethyl acetate. The organic layer was separated and the aqueous aqueous phase extracted with ethyl acetate (2×). The combined organic solutions were washed with water, dried (MgSO$_4$) and concentrated to give product 38 as an oil (200 mg). LCMS of 38 showed a mixture of boronic acid and its methyl ester.

1-(tert-Butyl-dimethyl-silanyl)-5-[2-(pyrimidin-2-yloxy)-phenyl]-1H-pyrrolo[2,3-b]pyridine (40)

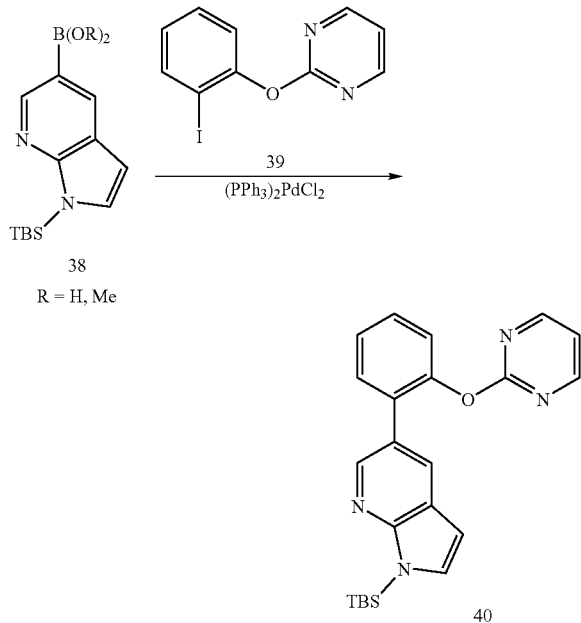

A mixture of 38 (100 mg, 0.36 mmol), iodide 39 (72 mg, 0.24 mmol), LiCl (31 mg, 0.72 mmol), PdCl$_2$(PPh$_3$)$_2$ (31 mg, 0.024), 1M aq. Na$_2$CO$_3$ (603 μL, 0.60 mmol) in toluene (1.66 mL) and EtOH (1.66 mL) was refluxed for 5 h. The reaction mixture was cooled, poured onto ethyl acetate/brine and the aqueous phase extracted with more ethyl acetate (2×). The combined organic solutions were dried (MgSO$_4$) and concentrated. The residue was partially purified by preparative TLC (4×1 mm, 60% ethyl acetate in hexane eluent) to give 40 (120 mg, 124%).

5-[2-(Pyrimidin-2-yloxy)-phenyl]-1H-pyrrolo[2,3-b]pyridine (41)

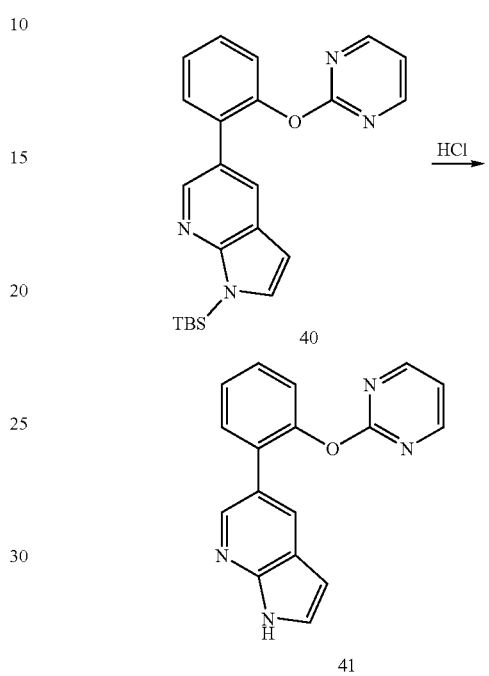

A mixture of 40 prepared above (120 mg, approx. 0.24 mmol), MeOH (1.1 mL) and 10% aq. HCl (2.4 mL) were stirred at room temperature for 1 h then poured onto saturated aq. NaHCO$_3$/ethyl acetate. The aqueous phase was extracted with more ethyl acetate and the combined organic extracts dried (MgSO$_4$) and concentrated to give pure product 41 (40.8 mg, 44% over 3 steps from 26); $^1$H NMR (400 MHz, CDCl$_3$) δ 6.40 (dd, J=3.4, 1.6 Hz, 1H), 6.76 (t, J=4.8 Hz, 1H), 7.21 (m, 2H), 7.32 (dt, J=7.8 Hz, 1.8 Hz, 1H), 7.39 (dt, J=7.8, 1.8 Hz, 1H), 7.46 (dd, J=7.5, 1.8 Hz, 1H), 8.04 (d, J=2.0 Hz, 1H), 8.30 (d, J=4.8 Hz, 2H), 8.37 (d, J=2.0 Hz, 1H), 10.26 (bs, NH).

Installation of stannane at C(5) of the 7-azaindole system via 5-lithio derivative.

Synthesis of 5-(hetero)aryl Derivative 43 Using Stille Reaction.

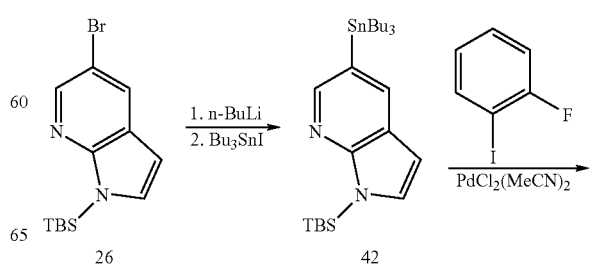

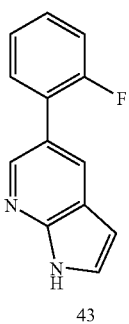

43

1-(tert-Butyl-dimethyl-silanyl)-5-tributylstannanyl-1H-pyrrolo[2,3-b]pyridine (42)

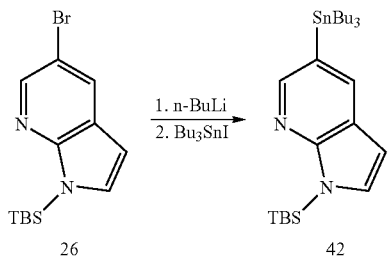

To 2.5 M n-BuLi in hexane (0.67 mL, 1.69 mmol) in THF (5 mL), cooled to −78° C., was added a solution of 26 (0.25 g, 0.80 mmol) in THF (1.0 mL) dropwise. The solution was stirred at −78° C. for 10 min then a solution of Bu₃SnI (446 mg, 0.96 mmol) in THF (0.5 mL) was added in one portion. The reaction mixture was stirred at −78° C. for 1 h then at room temperature for 2 h, then poured onto a mixture of ethyl acetate/saturated aq. NaHCO₃. The aqueous phase was extracted with more ethyl acetate (2×). The combined organic solutions were dried (MgSO₄) and concentrated to give stannane 42 as a light orange oil (483 mg, 115%); ¹H NMR (400 MHz, CDCl₃) δ 0.71 (s, 6H), 0.98 (t, J=7.4 Hz, 9H), 1.02 (s, 9H), 1.15-1.70 (m, 18H), 6.56 (d, J=3.5 Hz, 1H), 7.26 (d, J=3.5 Hz, 1H), 8.01 (d, J=1.4 Hz, 1H), 8.33 (d, J=1.4 Hz, 1H).

5-(3-Fluoro-phenyl)-1H-pyrrolo[2,3-b]pyridine (15)

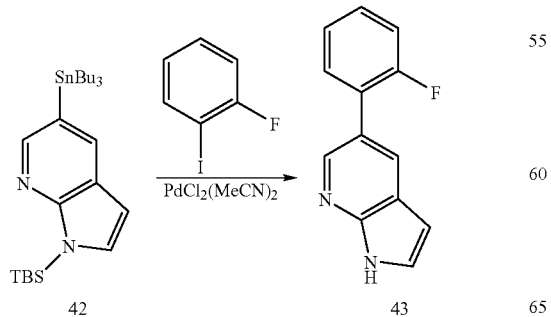

A mixture of stannane 42 (200 mg, 0.384 mmol), 1-fluoro-3-iodobenzene (170 mg, 0.767 mmol), PdCl₂(MeCN)₂, and P(o-tolyl)₃ in toluene (3.3 mL) were heated at 85° C. overnight. The reaction mixture was diluted with ethyl acetate, extracted with 10% aq. HCl (4×1 mL) and the HCl extracts basified with saturated aq. NaHCO₃, then extracted with ethyl acetate (3×). The combined organic extracts were dried (MgSO₄) and concentrated. Purification by preparative TLC (1 mm plate, 60% ethyl acetate in hexane eluent) afforded 43 (8.0 mg, 10%); ¹H NMR (400 MHz, CDCl₃) δ 6.57 (dd, J=3.5, 1.7 Hz, 1H), 7.06 (m, 1H), 8.13 (d, J=2.1 Hz, 1H), 7.34 (m, 1H), 7.42 (m, 3H), 8.56 (d, J=2.1 Hz, 1H), 10.66 (bs, NH).

Synthesis of Ketone 45

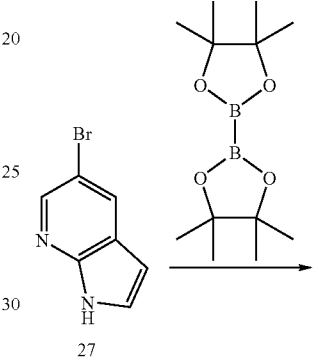

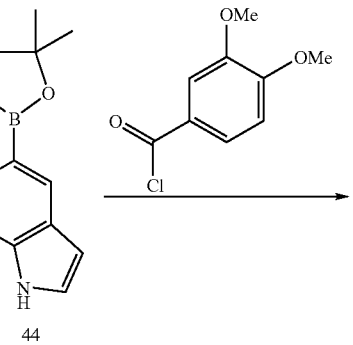

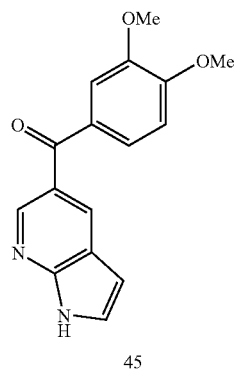

45

5-(4,4,5,5-Tetramethyl-[1,3,2]dioxaborolan-2-yl)-1H-pyrrolo[2,3-b]pyridine (44)

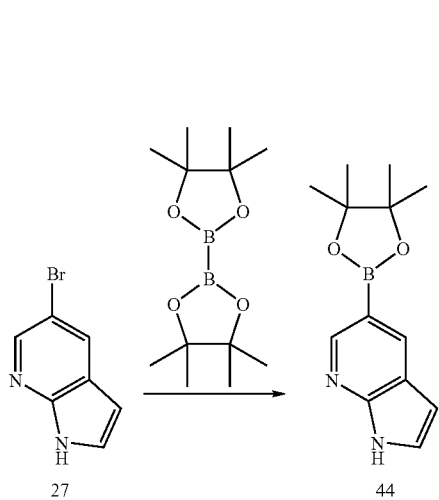

The 5-bromo-7-azaindole 27 (0.5 g, 2.54 mmol), bis(pinacolato)diboron (0.968 g, 3.81 mmol), potassium acetate (0.748 g, 7.61 mmol), [1,1'-bis(diphenylphosphino)ferrocene]dichloropalladium(II) complex with $CH_2Cl_2$ (1:1) (49 mg, 0.06 mmol) and DMF (11 mL) were heated in a sealed tube at 80° C. After 44 h, the reaction mixture was allowed to cool to room temperature, diluted with EtOAc and saturated brine, and partitioned. The aqueous layer was extracted with EtOAc (3×). The combined organic extracts were washed with brine (1×), dried ($MgSO_4$), filtered and concentrated in vacuo. The crude pinacol ester 44 was used directly for the next step without any further purification. $^1$H NMR (400 MHz; $CDCl_3$) δ 1.38 (s, 12H), 6.51 (d, J=3.5 Hz, 1H), 7.32 (d, J=3.5 Hz, 1H), 8.42 (d, J=1.2 Hz, 1H), 8.63 (d, J=1.2 Hz, 1H) and 10.59 (brs, NH).

(3,4-Dimethoxy-phenyl)-(1H-pyrrolo[2,3-b]pyridin-5-yl)-methanone (45)

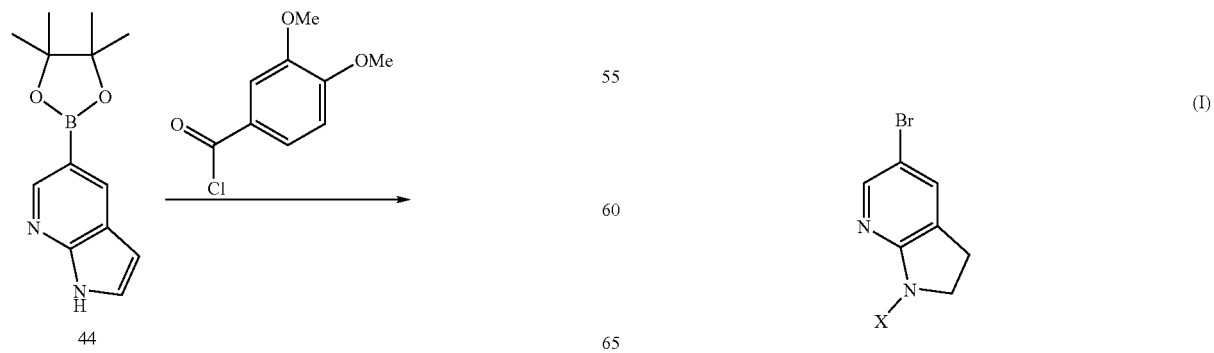

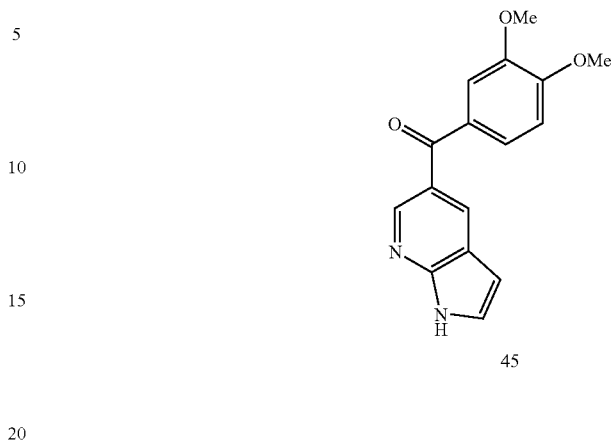

To the crude pinacol ester 44 (310 mg, 1.27 mmol) in dry toluene (25 mL) was sequentially added cesium carbonate (2.07 g, 6.35 mmol), tetrakis(triphenylphosphine)palladium (0) (73 mg, 0.06 mmol) and 3,4-dimethoxybenzoyl chloride (510 mg, 2.54 mmol). The mixture was heated at 100° C. in the dark. After 28 h a further portion of tetrakis(triphenylphosphine)palladium(0) (90 mg, 0.08 mmol) was added. Following another 22 h the mixture was allowed to cool to ambient temperature and diluted with EtOAc and water and partitioned. The organic layer was washed with saturated sodium hydrogen carbonate, saturated brine, dried ($MgSO_4$), filtered and concentrated. The crude residue was purified by preparative LCMS (column LUNA 10μ C18(2) 00G-4253-V0 250×50 mm) using water—acetonitrile (0.1% AcOH) as eluent (in gradient; flow 80 mL/min) to afford ketone 45 [12.6 mg, 3.6% (2 steps)] as a white solid. $^1$H NMR (400 MHz; $CDCl_3$) δ 3.99 (s, 3H), 4.00 (s, 3H), 6.54 (dd, J=2.0 and 3.5 Hz, 1H), 6.98 (d, J=8.5 Hz, 1H), 7.38 (dd, J=2.5 and 3.5 Hz, 1H), 7.71 (d, J=2.0 Hz, 1H), 7.81 (dd, J=0.7 and 2.5 Hz, 1H), 7.93 (dd, J=2.0 and 8.5 Hz, 1H), 8.22 (d, J=2.5 Hz, 1H) and 8.90 (brs, NH).

The invention claimed is:

1. A compound of formula (I)

wherein X is $R^1S(O)_2$, $(R^1)_3Si$, $R^1C(O)$, $R^1OCH_2$, $R^1_2NSO_2$, $R^1OC(O)-$, $R^1(R^1O)CH-$, $R^1CH_2CH_2-$, $R^1CH_2-$, $PhC(O)CH_2-$, $CH_2=CH-$, $ClCH_2CH_2-$, $Ph_3C-$, $Ph_2(4\text{-pyridyl})C-$, $Me_2N-$, $HO-CH_2-$, $R^1OCH_2-$, $(R^1)_3SiOCH_2-$, $(R^1O)_2CH-$, $t\text{-BuOC(O)}CH_2-$, $Me_2NCH_2-$ and tetrahydropyranylamine;

wherein $R^1$ is $C_{1-6}$ alkyl, $C_{3-12}$ cycloalkyl, $C_{1-6}$ haloalkyl, or $C_{6-12}$ carbocyclyl; optionally substituted with one or more of $C_{1-6}$ alkyl, $Si(R^3)_3$, $OR^3$, $NO_2$, $CO_2$, $CO_2R^3$, halogen, haloalkyl, $SR^3$, CN, $NR^3COR^3$, $COR^{13}CONR^3R^3$, wherein $R^3$ is hydrogen or $C_{1-6}$ alkyl, with the proviso that when X is $R^1OC(O)-$, $R^1$ is not $PhCH_2$.

2. The compound of claim 1, wherein X is $(R^1)_3Si$ or $R^1OCH_2$, and $R^1$ is $C_{1-6}$ alkyl or $C_{6-12}$ aryl.

3. The compound of claim 1, wherein X is $(R^1)_3Si$ and $R^1$ is methyl, ethyl, propyl, butyl or phenyl.

4. The compound of claim 1, wherein X is TBS.

5. The compound of claim 1, wherein X is $PhSO_2$.

6. A method for synthesizing a compound of formula (I) as claimed in claim 2, comprising brominating a compound of formula (II);

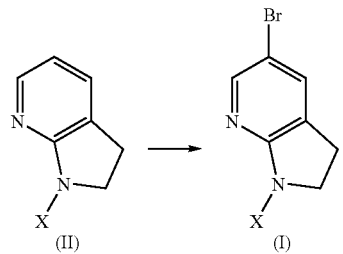

wherein X is $(R^1)_3Si$ or $R^1OCH_2$, and $R^1$ is $C_{1-6}$ alkyl or $C_{6-12}$ aryl.

7. A method as claimed in claim 6 wherein the bromination is carried out using $Br_2$, dioxane dibromide, pyridinium perbromide or NBS.

8. A method as claimed in claim 6 wherein X is $(R^1)_3Si$ and $R^1$ is methyl, ethyl, propyl, butyl or phenyl.

9. A method as claimed in claim 7 wherein X is $(R^1)_3Si$ and $R^1$ is methyl, ethyl, propyl, butyl or phenyl.

* * * * *

UNITED STATES PATENT AND TRADEMARK OFFICE
CERTIFICATE OF CORRECTION

PATENT NO. : 7,652,137 B2
APPLICATION NO. : 10/548162
DATED : January 26, 2009
INVENTOR(S) : Graczyk et al.

It is certified that error appears in the above-identified patent and that said Letters Patent is hereby corrected as shown below:

On the title page,

[*] Notice:   Subject to any disclaimer, the term of this patent is extended or adjusted under 35 USC 154(b) by 450 days.

Delete the phrase "by 450 days" and insert -- by 851 days --

Signed and Sealed this

Sixth Day of July, 2010

David J. Kappos
*Director of the United States Patent and Trademark Office*